United States Patent [19]

Halbert et al.

[11] Patent Number: 4,730,064

[45] Date of Patent: Mar. 8, 1988

[54] HETEROMETALLIC THIOCUBANES (C-2044)

[75] Inventors: Thomas R. Halbert, Annandale, N.J.; Steven A. Cohen, Naperville, Ill.; Edward I. Stiefel, Bridgewater, N.J.

[73] Assignee: Exxon Research and Engineering Company, Florham Park, N.J.

[21] Appl. No.: 870,772

[22] Filed: Jun. 2, 1986

Related U.S. Application Data

[63] Continuation-in-part of Ser. No. 711,601, Mar. 14, 1985, abandoned.

[51] Int. Cl.[4] .................. C07F 15/00; C07F 15/02; C07F 15/04; C07F 15/06

[52] U.S. Cl. .................................... 556/15; 556/14; 556/16; 556/28; 556/31

[58] Field of Search ............... 556/14, 15, 16, 28, 556/31

[56] References Cited

U.S. PATENT DOCUMENTS

| | | |
|---|---|---|
| 2,909,541 | 10/1959 | Hugel . |
| 2,951,040 | 8/1960 | Hugel et al. . |
| 3,068,259 | 12/1962 | Hartle . |
| 3,356,702 | 12/1967 | Farmer et al. . |
| 3,400,140 | 9/1968 | Rowan et al. . |
| 3,402,188 | 9/1968 | Wiese . |
| 3,419,589 | 12/1968 | Larson et al. . |
| 3,480,563 | 11/1969 | Bonetti et al. . |
| 3,867,417 | 2/1975 | Gleim et al. . |
| 4,098,705 | 7/1978 | Sakurai et al. ............ 556/38 X |
| 4,203,999 | 5/1980 | Martin et al. ............ 556/31 X |
| 4,208,292 | 6/1980 | Bridger . |
| 4,259,254 | 3/1981 | Bridger . |
| 4,290,902 | 9/1981 | Levine et al. . |
| 4,315,826 | 2/1982 | Schlicht et al. . |
| 4,428,861 | 1/1984 | Bridger . |
| 4,551,543 | 11/1985 | Doyle et al. ............. 556/31 X |

OTHER PUBLICATIONS

Mak et al., Angew. Chem. Int. Ed. Engl., 23, pp. 391–392, (1984).
Shibahara et al., J. Am. Chem. Soc., 106, pp. 789–791, (1984).
Chu et al., J. Am. Chem. Soc., 104, pp. 3409–3422, (1982).
Simon et al., J. Am. Chem. Soc., 95, pp. 2164–2174, (1973).
Curtis et al., Inorg. Chem., 22, pp. 2661–2662.
Brunner et al., J. Organometallic Chem., 240, C41–C44, (1982).
Holm, Chem. Soc. Rev., 10, 455, (1981).
Armstrong et al., Inorg. Chem., 21, 1699–1701, (1982).
Gates et al., "Chemistry of Catalytic Processes", McGraw Hill, New York, pp. 390–445, (1979).
Inorganic Chemistry, Dec. 1985, 24, 4657–4662.
Organo Metallics, 1985, 4, 1689–1690.

Primary Examiner—Helen M. S. Sneed
Attorney, Agent, or Firm—E. Thomas Wheelock; Joseph J. Dvorak

[57] ABSTRACT

This invention relates to heterometallic thiocubane compositions containing the $M_2^1M_2^2S_4$ cluster core and methods of making them wherein $M^1$ is Re, V, Mo or W and $M^2$ is Co, Cr, Cu, Ni or Fe but preferably Co. More particularly, the invention relates to compositions of the formula $M_2^2M_2^2S_4L_2^1L_2^2L_2^3$ wherein $M^1$ and $M^2$ are as above, $L^1$ is a bidentate sulfur or nitrogen bearing ligand (most preferably a dialkyldithiocarbamate), $L^2$ is optional but may be an O, N, P or S-containing monodentate donor ligand, and $L^3$ may be CO, a monodentate anion ligand such as a halide (preferably Cl), mercaptide or alkoxide, or another O, N, P, or S containing monodentate donor ligand. The compositions are suitable for making active hydrotreating catalysts.

27 Claims, 2 Drawing Figures

HETEROMETALLIC THIOCUBANES (C-2044)

CROSS-REFERENCE TO RELATED APPLICATIONS

This application is a continuation-in-part of U.S. Ser. No. 711,601, filed Mar. 14, 1985 now abandoned.

FIELD OF THE INVENTION

This invention relates to heterometallic thiocubane compositions containing the $M_2^1M_2^2S_4$ cluster core and methods of making them wherein $M^1$ is Re, V, Mo or W but preferably Mo or W; and $M^2$ is Co, Cr, Cu, Ni, or Fe but preferably Co. More particularly, the invention relates to compositions of the formula $M_2^1M_2^2S_4L_2^1L_2^2L_2^3$ wherein $M^1$ and $M^2$ are as above, $L^1$ is a bidentate sulfur and/or nitrogen bearing ligand (desirably a dithiolate and preferably a dialkyldithiocarbamate), $L^2$ is optional and may be an O, N, P, or S-containing monodentate donor ligand, and $L^3$ may be CO, a monodentate anion ligand such as a halide (preferably Cl), mercaptide or alkoxide, or another O, N, P, or S containing monodentate donor ligand. The compositions are suitable for making active hydrotreating catalysts.

BACKGROUND OF THE INVENTION

Thiocubane clusters containing a homometallic core $M_4S_4$ are known in the art. The thiocubane core is so-named because of its molecular architecture, i.e., two tetrahedra of metal and sulfur atoms interlock so that the metal atoms and bridging sulfurs occupy the alternate corners of a distorted or approximate cube. Homometallic thiocubane structures containing, e.g., Co, Fe, Mo, have been synthesized and discussed at length in the chemical literature. See, e.g., Mak et al, Angew. Chem. Int. Ed. Engl. 23 (1984), pp. 391-2; shibahara et al, J. Am. Chem. Soc. (1984), 106, pp. 789-791; Chu et al, J. Am. Chem. Soc. (1982), v. 104, pp. 3409-3422 (and references cited therein) and Simon et al, J. Am. Chem. Soc. (1973), v. 95, pp. 2164-2174.

Compositions containing heterometallic thiocubane clusters have also been studied. The particular interest in the $Fe_2MoS_4$ cluster, because of its possible function as the biologically active part of nitrogenase, has led to the attempted synthesis of other similar compositions. See, e.g., Curtis et al, Inorg. Chem., v. 22, pp. 2661-2; Brunner et al, Agnew. Chem. Int. Ed. Engl 22 (1983), pg. 549; Brunner et al, J. Organometallic Chem., 240 (1982) C41-C44; Holm, Chem. Soc. Rev. (1981), v. 10, p. 455; and Armstrong et al., Inorg. Chem. (1982) v. 21, 1699-1701.

In addition to the interest shown in the bimetallic thiocubane cluster as a biologically active enzyme constituent, others have suggested that sulfided clusters containing molybdenum and a Group VIII metal, e.g., Fe, Co or Ni, may be useful as models in clarifying the somewhat poorly understood activity of hydrodesulfurization catalysts based on "sulfided" iron, cobalt, or nickel molybdates and tungstates on oxide supports. See, Curtis et al, supra, and the references cited therein; Gates et al, "Chemistry of Catalytic Processes", McGraw-Hill, New York (1979), pp. 390-445.

In the earlier syntheses of the thiocubane core, the approach was typically "spontaneous assembly". See, Holm, supra. Later work in homometallic transition metal sulfide chemistry led to smaller clusters which could be considered fragments of the thiocubane unit. These fragments, e.g., $Cp_2M_2S_4$ and related compounds (where Cp represents the cylcopentadienyl ligand), are potential building blocks for heteronuclear thiocubane clusters and can be used to form clusters with $M_2M_2'(\mu^3-S)_4$ cores. See, the two Brunner et al articles, supra.

None of the prior art shows the synthesis of $M_2^1M_2^2(\mu^3-S)_4L_2^1L_2^2L_2^3$ where $M^1$ is Re, V, Mo or W, $M^2$ is Co, Cr, Cu, Ni or Fe, $L^1$ is a bidentate sulfur and/or nitrogen bearing ligand, and $L^2$ is optional but may be an S, N, P, or O monodentate donor ligand, e.g., a solvent or other Lewis base molecule, and $L^3$ may be CO, a monodentate anion ligand such as a halide (preferably Cl), mercaptide or alkoxide, or another O, N, P, or S containing monodentate donor ligand.

SUMMARY OF THE INVENTION

This invention deals with compositions containing heterometallic thiocubane nuclei. In particular the compositions have the generalized formula $M_2^1M_2^2(\mu^3-S)_4L_2^1L_2^2L_2^3$ where $M^1$ is Re, V, Mo or W (but preferably Mo or W); $M^2$ is Co, Cr, Cu, Ni or Fe (but preferably Co); $L^1$ is a bidentate sulfur and/or nitrogen bearing ligand such as dithiolates and particularly xanthate, o-aminobenzenethiolate, dithiophosphinate, dithiophosphate (but preferably a dithiocarbamate ($S_2CNR_2$) where R is independently H, or a hydrocarbyl such as methyl, ethyl, propyl, butyl, phenyl or mixtures of such groups, but preferably ethyl); $L^2$ is optional but may be an S, N, P, or O monodentate donor ligand, e.g., a solvent or other Lewis base molecule such as a pyridine, ether or phosphine ligand (but is preferably acetonitrile); and $L^3$ may be CO, a monodentate anion ligand such as a halide (preferably Cl), mercaptide or alkoxide, or another O, N, P, or S containing monodentate donor ligand.

The heterometallic thiocubane composition is preferably synthesized using novel dimeric neutral complexes of, e.g., tungsten, sulfide and dialkyldithiocarbamates.

The heterometallic thiocubane compositions have various uses but are especially useful in the preparation of catalysts for hydrotreating hydrocarbons containing sulfur-bearing compounds.

DESCRIPTION OF THE INVENTION

Figure 1:
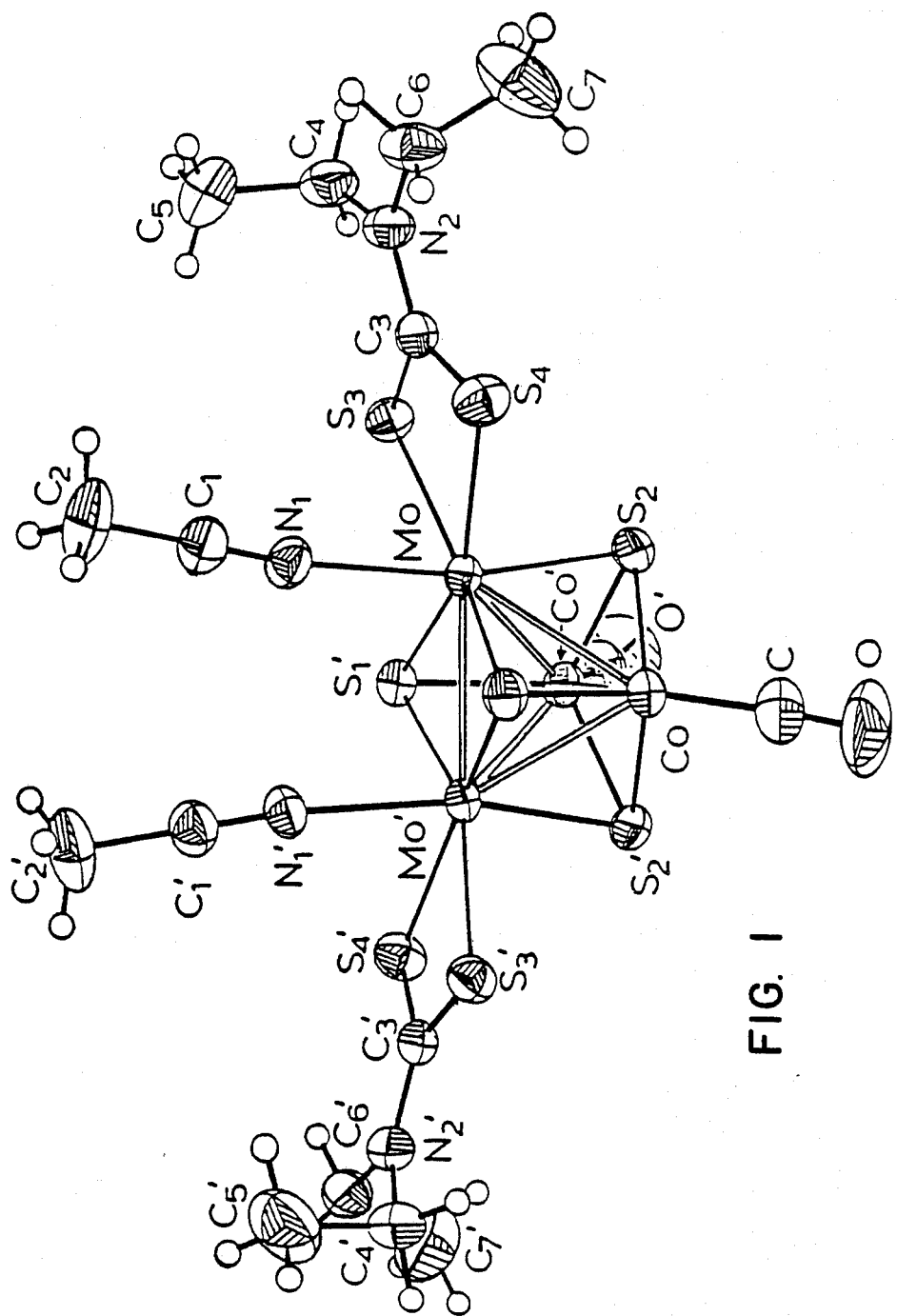
FIG. 1 is a molecular depiction of one composition, i.e., $Mo_2Co_2(\mu^3-S)_4((C_2H_5)_2NCS_2)_2(CO)_2(CH_3CN)_2$, within the scope of the invention.

The invention, as noted above, is generically a composition of matter containing certain heterometallic thiocubane clusters. The broad formula for the composition is:

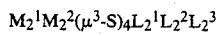

where:
$M^1$ is Re, V, Mo or W; preferably Mo or W;
$M^2$ is Co, Cr, Cu, Ni or Fe; preferably Co;
$L^1$ is a bidentate sulfur and/or nitrogen-bearing ligand such as amino benzene thiolate or dithiolates, particularly xanthate, dithiophosphinate, dithiophosphate, dithiocarbamate, etc.; preferably dithiocarbamate ($S_2CNR_2$) where R is independently an H or a hydrocarbyl, such as methyl, ethyl, propyl, butyl, phenyl, most preferably ethyl; other suitable ligands include those having the formula: $C_6H_4SNH_2$, $SCH_2CH_2S$, and $CH_3NHCH_2(CH_3)_2S$.

$L^2$ is optional but may be a monodentate S, N, P, or O donor ligand, e.g., a solvent or other Lewis base molecule such as a pyridine, ether or phosphine but preferably acetonitrile. The thiocubane core is, however, stable without the presence of $L^2$.

$L^3$ may be CO, a monodentate anion ligand such as a halide (preferably Cl), mercaptide or alkoxide, or another O, N, P, or S containing monodentate donor ligand.

The preferred method of synthesizing the inventive heterometallic thiocubanes involves the addition of a generally stoichiometric amount of a low valent complex based upon one of the "$M^2$" metals Co, Cr, Cu, Ni or Fe such as $Co_2(CO)_8$, $Ni(CO)_4$, or CuCl to a solution or slurry of $M_2^1S_4L_2^1$. The metal $M^1$, as above, may be Re, V, Mo or W although preferably is Mo or W. To achieve the goal of including substantial sulfur in a hydrodesulfurization catalyst using the inventive compound as a precursor, the bidentate ligand should be a mono- or a dithiolate. Although a large number of such ligands may be used, e.g., amino benzene thiolates, xanthates, dithiophosphinates, dithiophosphates, the preferred ligand is a dithiocarbamate of the formula $S_2CNR_2$ wherein R is independently H or a hydrocarbyl or alkyl of $C_1$ to $C_{12}$. The diethyl form is especially preferred.

These two materials may be placed together in a suitable solvent which may, by default, act as the monodentate ligand $L^2$ (or $L^3$) above. Acetonitrile is especially useful.

These "inorganic synthons" obviously act as building blocks to the final inventive heterometallic thiocubane composition. The reaction usually proceeds at room temperature with no heat input required.

Although the syntheses of a majority of the materials used in producing the thiocubanes are known, the production of one such fragment is not, i.e., $W_2S_4(S_2CNR_2)_2$ where R is an H or a $C_1$ to $C_{12}$ hydrocarbyl group.

These fragments may be made by gently heating $(NEt_4)_2W_2S_{12}$ in an acetonitrile solution, or other aprotic solvent, in the presence of $R_2NCS_2^-$, $NH_4^+$, and $P(C_6H_5)_3$. When making the tungsten-based compound, the product is found in and may be isolated from an orange slurry.

This process may be used to produce compounds of the formula:

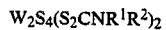

where $R^n$ = H, an alkyl of 1 to 12 carbon atoms, and aryl groups of 6 to 12 carbamates. $R^1$ need not be the same as $R^2$ and also

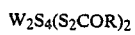

where R are alkyl or aryl groups of the type discussed above.

Having thus described the invention in detail, following are a number of examples which further delineate the invention. These examples are not intended to be limiting in any manner to the invention claimed below.

EXAMPLE 1

Production of $(NEt_4)_2W_2S_{12}$

Excess sulfur (1.18 g, 4.60 mmol) was added to a stirred solution of $(NH_4)_2WS_4$ (3.20 g, 9.20 mmol) in 50 mL DMF and heated two hours at 110° while purging slowly with Ar. The resulting orange-red solution was allowed to cool, excess $NEt_4Br$ (2.55 g, 12.1 mmol) was added, and the mixture heated at 110° for an additional 60 min. Volatiles were removed at 60° under vacuum, leaving an oily orange-red solid. Repeated recrystallization of the product from acetonitrile with intermittent washings with toluene, methanol, and diethylether yielded 3.85 g (83%) of red crystalline $(NEt_4)_2W_2S_{12}$.

Anal. Calcd for $C_{16}H_{40}N_2S_{12}W_2$: C, 18.97, H, 3.98, N, 2.77, S, 37.98, W, 36.30. Found: C, 19.00, H, 3.86, N, 2.68, S, 37.44, W. 36.25. IR: 3000 (w), 2980 (w), 1474 (s), 1445 (m), 1432 (m), 1417 (w), 1390 (m), 1385 (m), 1312 (m), 1184 (w), 1168 (s), 1065 (w), 1049 (w), 996 (s), 777 (s), 506 (vs), 495 (sh), 460 (w), 423 (m), 414 (m), 405 (sh), 380 (m), 371 (w), 294 (m) $cm^{-1}$. FAB-MS (in tetramethylenesulfone) m/e for parent negative ion $[(NEt_4)W_2S_{12}]^-$ (rel. abundance calc, exp): 878 (19,25); 879 (23,28); 880 (62,62); 881 (45,51); 882 (100,100), 883 (55,61); 884 (96,98); 885 (32,42); 886 (60,62); 887 (14,19); 888 (21,25). $^{183}W$ NMR (1.11 g $(NEt_4)_2W_2S_{12}$ in 2.2 mL DMF and 0.7 mL DMF-$d_7$): 2131.

EXAMPLE 2

Production of $W_2S_4(S_2CNEt_2)_2$

An acetonitrile solution of (50 ml) containing $PPh_3$ (0.8 g, 3 mmol), $NH_4PF_6$ (0.48 g, 2.9 mmol), $Na(S_2CNEt_2)\cdot 3H_2O$ (0.35 g, 1.6 mmol), and $(NEt_4)_2W_2S_{12}$ (0.508 g, 0.502 mmol) made according to Example 1 was heated at 75° for 45 min., resulting in the formation of an orange slurry. Volatiles were removed in vacuo, leaving a mixture of orange and white solids. The mixture was cooled to 0° and washed with $2\times15$ ml $CH_3OH$, $2\times20$ ml acetone, and $3\times20$ ml ether. The resulting orange powder was dried under vacuum. Yield was 300 mg (75%). Air-stable $W_2S_4(S_2CNEt_2)_2$ is very slightly soluble in DMF and hot acetonitrile.

Anal. Calcd. for $C_{10}H_{20}N_2S_8W_2$: C, 15.16; H, 2.54; N, 3.53; S, 32.36. Found: C, 14.94; H, 2.30; N, 3.57; S, 32.34. IR: 2980 (w), 2935 (w), 1530 (s), 1456 (m), 1440 (m), 1382 (w), 1358 (m), 1297 (w), 1281 (s), 1201 (m), 1152 (m), 1098 (w), 1077 (m), 1006 (w), 996 (w), 908 (w), 847 (w), 779 (w), 527 (s), 519 (s), 445 (m), 371 (m), 323 (m) $cm^{-1}$. Field desorption mass spectrum m/e for parent $W_2S_8C_{10}H_{20}N_2$, relative abundance (calc., exp.): 788 (21,21); 789 (26,24); 790 (66,68); 791 (46,43); 792 (100,100); 793 (52,60); 794 (89,79); 795 (26,32); 796 (50,41).

EXAMPLE 3

Production of $W_2S_4(S_2CN(i\text{-}C_4H_9)_2)_2$

The procedure of Example 2 was repeated using $Na(S_2CN(i\text{-}C_4H_9)_2)$ instead of the diethyl analog. The resulting product had characteristic IR bands at 535, 523, 448, 372 and 328 $cm^{-1}$ (all $\pm 5$ $cm^{-1}$).

EXAMPLE 4

Production of $(Et_2NCS_2)_2(MeCN)_2W_2(\mu^3\text{-}S)_4Co_2(CO)_2$

In an inert atmosphere glove box, solid $Co_2(CO)_8$ (0.505 g, 1.48 mmol) was added over a period of five minutes to a stirred orange slurry of $W_2S_4(S_2CNEt_2)_2$ (1.175 g, 1.49 mmol) in 80 ml acetonitrile as made according to Example 2. The solution darkened to a brown-black slurry as gas was evolved. The mixture was stirred 2 hours and then filtered. The filtrate was concentrated to ca. 60 ml and placed in a $-10°$ freezer overnight. Black crystalline $(Et_2NCS_2)_2$-$(MeCN)_2W_2(\mu^3\text{-}S)_4Co_2(CO)_2$ was filtered from the dark solution on a sintered-glass Schlenk filter, washed with 8 mL acetonitrile, and dried in vacuo. Yield was 650 mg (42%).

Anal. Calcd. for $C_{16}H_{26}N_4O_2S_8Co_2W_2$: C, 18.33; H, 2.50; N, 5.34; W, 35.07. Found: C, 18.03; H, 2.49; N, 5.27; W, 35.27. IR (KBr pellet): 1961 (s), 1938 (s), 1505 (s), 1456 (w), 14.36 (m), 1358 (w), 1300 (w), 1273 (m), 1209 (m), 1147 (m), 1095 (w), 1075 (m), 915 (w), 847 (w), 783 (w), 521 (m), 394 (w), and 368 (w) cm$^{-1}$.

EXAMPLE 5

Production of $(Et_2NCS_2)_2(MeCN)_2Mo_2(\mu^3\text{-}S)_4Co_2(CO)_2$

In an inert atmosphere glove box, solid $Co_2(CO)_8$ (sublimed, 0.111 g, 0.324 mmoles) was added over a period of several minutes to a stirred slurry of red-brown $Mo_2S_4(S_2CNEt_2)_2$ (0.200 g, 0.324 mmoles) in 20 ml dry $CH_3CN$ (distilled from $CaH_2$). This material was made via the process disclosed in Miller et al, J. Am. Chem. Soc. (1980), pp. 5104–5106. The solution darkened rapidly with gentle evolution of carbon monoxide. After stirring for two hours, the solution was filtered and the dark black-brown filtrate was concentrated under vacuum to a volume of 5 ml. The mixture was then allowed to stand 18 hours. Black crystalline $(Et_2NCS_2)_2(MeCN)_2Mo_2(\mu^3\text{-}S)_4Co_2(CO)_2$ was filtered on a medium porosity sintered glass frit, and dried in vacuo. Yield was 200 mg (71%).

IR spectrum (KBr pellet): 1983 (s), 1960 (s), 1505 (s), 1465 (m), 1442 (m), 1385 (w), 1368 (m), 1310 (w), 1280 (s), 1220 (m), 1152 (m), 1103 (w), 1083 (m), 1008 (w), 976 (w), 922 (w), 851 (w), 790 (w), 578 (w), 521 (m), 498 (w), 436 (vw), 401 (w), 371 (m). Anal. Calcd. for $C_{16}H_{26}N_4O_2S_8Co_2Mo_2$: C, 22.02; H, 3.00; N, 6.42; 1 Mo, 21.99; Co, 13.51. Found C, 18.59; H, 2.83; N, 5.11; Mo, 21.10; Co, 14.22.

A single crystal x-ray diffraction study was carried out on the product. The structure is illustrated in FIG. 1 and the x-ray structure factors are given in Table 1. The molecule contains a $Co_2Mo_2(\mu^3\text{-}S)_4$ core. The four metal atoms are joined by six metal-metal bonds forming an approximate tetrahedron of $C_{2v}$ symmetry. Each triangular face of the tetrahedron is capped by a sulfur, to form the overall "thiocubane" core. Each cobalt is further bonded to a single terminal CO. The coordination environment about the cobalt atoms (discounting the M-M bonds) very nearly tetrahedral. Each molybdenum atom is bound to tow dithiocarbamate sulfur atoms and to the nitrogen of an acetonitrile molecule, in addition to three capping "$\mu^3$-S" atoms. The coordination environment about the molybdenum atoms is distorted octahedral. The molecule resides on a crystallographic $C_2$ axis which bisects the Mo-Mo' and Co-Co' bonds.

TABLE 1

$MO_2CO_2S_4(CO)_2(NCCH_3)_2[S_2CH(C_2H_5)_2]_2$

| H | K | L | FOBS | FCAL | H | K | L | FOBS | FCAL |
|---|---|---|------|------|---|---|---|------|------|
| 2 | 0 | 0 | 4951 | 4967 | 20 | 4 | 0 | 202 | 192 |
| 4 | 0 | 0 | 1638 | 1654 | 24 | 4 | 0 | 295 | 289 |
| 6 | 0 | 0 | 2661 | 2633 | 1 | 5 | 0 | 2267 | 2247 |
| 8 | 0 | 0 | 5917 | 5956 | 3 | 5 | 0 | 2207 | 2178 |
| 10 | 0 | 0 | 4832 | 4831 | 5 | 5 | 0 | 206 | 190 |
| 12 | 0 | 0 | 2120 | 2099 | 7 | 5 | 0 | 1914 | 1887 |
| 14 | 0 | 0 | 641 | 656 | 9 | 5 | 0 | 1668 | 1658 |
| 16 | 0 | 0 | 679 | 675 | 11 | 5 | 0 | 1846 | 1841 |
| 18 | 0 | 0 | 1518 | 1511 | 13 | 5 | 0 | 674 | 685 |
| 20 | 0 | 0 | 1127 | 1119 | 15 | 5 | 0 | 212 | 102 |
| 22 | 0 | 0 | 637 | 626 | 17 | 5 | 0 | 776 | 776 |
| 24 | 0 | 0 | 566 | 543 | 19 | 5 | 0 | 728 | 719 |
| 1 | 1 | 0 | 1089 | 1082 | 21 | 5 | 0 | 623 | 623 |
| 3 | 1 | 0 | 968 | 959 | 23 | 5 | 0 | 217 | 231 |
| 5 | 1 | 0 | 793 | 797 | 0 | 6 | 0 | 3088 | 3042 |
| 7 | 1 | 0 | 604 | 618 | 2 | 6 | 0 | 2843 | 2796 |
| 9 | 1 | 0 | 1777 | 1775 | 4 | 6 | 0 | 362 | 366 |
| 11 | 1 | 0 | 476 | 462 | 6 | 6 | 0 | 668 | 675 |
| 13 | 1 | 0 | 187 | 206 | 8 | 6 | 0 | 1851 | 1839 |
| 15 | 1 | 0 | 451 | 439 | 10 | 6 | 0 | 2127 | 2112 |
| 17 | 1 | 0 | 274 | 263 | 12 | 6 | 0 | 1091 | 1107 |
| 19 | 1 | 0 | 520 | 526 | 14 | 6 | 0 | 489 | 491 |
| 27 | 1 | 0 | 244 | 222 | 18 | 6 | 0 | 692 | 707 |
| 0 | 2 | 0 | 1656 | 1650 | 20 | 6 | 0 | 564 | 558 |
| 2 | 2 | 0 | 2666 | 2658 | 22 | 6 | 0 | 574 | 579 |
| 4 | 2 | 0 | 836 | 829 | 24 | 6 | 0 | 502 | 504 |
| 6 | 2 | 0 | 344 | 349 | 1 | 7 | 0 | 150 | 102 |
| 8 | 2 | 0 | 1955 | 1974 | 3 | 7 | 0 | 802 | 807 |
| 10 | 2 | 0 | 1651 | 1632 | 5 | 7 | 0 | 599 | 596 |
| 12 | 2 | 0 | 827 | 802 | 7 | 7 | 0 | 320 | 314 |
| 14 | 2 | 0 | 289 | 294 | 9 | 7 | 0 | 316 | 307 |
| 16 | 2 | 0 | 115 | 126 | 11 | 7 | 0 | 643 | 668 |
| 18 | 2 | 0 | 590 | 594 | 13 | 7 | 0 | 1342 | 1364 |
| 20 | 2 | 0 | 503 | 490 | 15 | 7 | 0 | 258 | 264 |
| 22 | 2 | 0 | 353 | 349 | 17 | 7 | 0 | 527 | 523 |
| 24 | 2 | 0 | 268 | 278 | 21 | 7 | 0 | 486 | 484 |
| 1 | 3 | 0 | 3046 | 3044 | 23 | 7 | 0 | 268 | 269 |
| 3 | 3 | 0 | 974 | 932 | 0 | 8 | 0 | 192 | 184 |
| 5 | 3 | 0 | 828 | 811 | 2 | 8 | 0 | 333 | 309 |
| 7 | 3 | 0 | 1481 | 1509 | 4 | 8 | 0 | 510 | 526 |
| 9 | 3 | 0 | 1836 | 1815 | 6 | 8 | 0 | 609 | 595 |
| 11 | 3 | 0 | 353 | 338 | 8 | 8 | 0 | 292 | 272 |
| 13 | 3 | 0 | 730 | 726 | 10 | 8 | 0 | 226 | 188 |
| 15 | 3 | 0 | 479 | 461 | 12 | 8 | 0 | 746 | 752 |
| 17 | 3 | 0 | 935 | 926 | 14 | 8 | 0 | 132 | 145 |
| 19 | 3 | 0 | 708 | 713 | 16 | 8 | 0 | 327 | 335 |
| 23 | 3 | 0 | 129 | 139 | 18 | 8 | 0 | 283 | 277 |
| 0 | 4 | 0 | 4682 | 4724 | 20 | 8 | 0 | 563 | 562 |
| 2 | 4 | 0 | 1863 | 1869 | 22 | 8 | 0 | 476 | 470 |
| 4 | 4 | 0 | 662 | 642 | 1 | 9 | 0 | 1706 | 1695 |
| 6 | 4 | 0 | 359 | 349 | 3 | 9 | 0 | 998 | 989 |
| 8 | 4 | 0 | 2656 | 2596 | 5 | 9 | 0 | 404 | 409 |
| 10 | 4 | 0 | 2096 | 2117 | 7 | 9 | 0 | 1276 | 1284 |
| 12 | 4 | 0 | 346 | 339 | 9 | 9 | 0 | 1452 | 1431 |
| 14 | 4 | 0 | 259 | 263 | 11 | 9 | 0 | 884 | 873 |
| 18 | 4 | 0 | 622 | 612 | 13 | 9 | 0 | 164 | 185 |
| 15 | 9 | 0 | 562 | 566 | -10 | 2 | 1 | 1180 | 1147 |
| 17 | 9 | 0 | 655 | 670 | -8 | 2 | 1 | 811 | 801 |
| 19 | 9 | 0 | 490 | 496 | -6 | 2 | 1 | 1215 | 1254 |
| 0 | 10 | 0 | 820 | 824 | -4 | 2 | 1 | 1016 | 972 |
| 2 | 10 | 0 | 451 | 473 | -2 | 2 | 1 | 2168 | 2199 |
| 8 | 10 | 0 | 260 | 267 | 0 | 2 | 1 | 477 | 460 |
| 10 | 10 | 0 | 291 | 312 | 2 | 2 | 1 | 2305 | 2244 |
| 14 | 10 | 0 | 248 | 267 | 4 | 2 | 1 | 659 | 649 |
| 16 | 10 | 0 | 272 | 298 | 6 | 2 | 1 | 860 | 891 |
| 1 | 11 | 0 | 1141 | 1134 | 8 | 2 | 1 | 981 | 1021 |
| 3 | 11 | 0 | 1036 | 1046 | 10 | 2 | 1 | 174 | 188 |
| 5 | 11 | 0 | 182 | 179 | 12 | 2 | 1 | 387 | 395 |
| 7 | 11 | 0 | 629 | 642 | 16 | 2 | 1 | 675 | 654 |
| 9 | 11 | 0 | 604 | 610 | 18 | 2 | 1 | 1529 | 1476 |
| 11 | 11 | 0 | 1066 | 1064 | 20 | 2 | 1 | 586 | 574 |
| 13 | 11 | 0 | 1007 | 1006 | 22 | 2 | 1 | 517 | 493 |
| 15 | 11 | 0 | 177 | 200 | 26 | 2 | 1 | 807 | 757 |
| 0 | 12 | 0 | 399 | 406 | -23 | 3 | 1 | 210 | 219 |
| 2 | 12 | 0 | 372 | 397 | -19 | 3 | 1 | 383 | 356 |
| 4 | 12 | 0 | 214 | 239 | -17 | 3 | 1 | 395 | 391 |
| 6 | 12 | 0 | 372 | 360 | -13 | 3 | 1 | 241 | 224 |

TABLE 1-continued
MO2CO2S4(CO)2(NCCH3)2[S2CH(C2H5)2]2

| H | K | L | FOBS | FCAL | H | K | L | FOBS | FCAL | H | K | L | FOBS | FCAL | H | K | L | FOBS | FCAL |
|---|---|---|------|------|---|---|---|------|------|---|---|---|------|------|---|---|---|------|------|
| 8 | 12 | 0 | 429 | 453 | −11 | 3 | 1 | 623 | 614 | 12 | 6 | 1 | 1108 | 1082 | 11 | 9 | 1 | 591 | 591 |
| 10 | 12 | 0 | 314 | 295 | −9 | 3 | 1 | 1252 | 1209 | 14 | 6 | 1 | 278 | 281 | 13 | 9 | 1 | 614 | 603 |
| 12 | 12 | 0 | 349 | 360 | −7 | 3 | 1 | 111 | 104 | 16 | 6 | 1 | 212 | 193 | 15 | 9 | 1 | 1013 | 1017 |
| 1 | 13 | 0 | 210 | 216 | −5 | 3 | 1 | 740 | 733 | 18 | 6 | 1 | 185 | 195 | 17 | 9 | 1 | 658 | 645 |
| 3 | 13 | 0 | 317 | 317 | −3 | 3 | 1 | 618 | 611 | 20 | 6 | 1 | 308 | 328 | 19 | 9 | 1 | 629 | 613 |
| 5 | 13 | 0 | 249 | 260 | −1 | 3 | 1 | 2024 | 1997 | −23 | 7 | 1 | 430 | 418 | −18 | 10 | 1 | 303 | 315 |
| 9 | 13 | 0 | 193 | 207 | 1 | 3 | 1 | 221 | 231 | −21 | 7 | 1 | 386 | 403 | −14 | 10 | 1 | 718 | 735 |
| −25 | 1 | 1 | 348 | 338 | 3 | 3 | 1 | 267 | 254 | −19 | 7 | 1 | 228 | 254 | −12 | 10 | 1 | 1051 | 1037 |
| −23 | 1 | 1 | 389 | 394 | 5 | 3 | 1 | 440 | 431 | −15 | 7 | 1 | 434 | 468 | −10 | 10 | 1 | 1014 | 1007 |
| −21 | 1 | 1 | 666 | 676 | 7 | 3 | 1 | 443 | 433 | −13 | 7 | 1 | 668 | 701 | −8 | 10 | 1 | 976 | 907 |
| −19 | 1 | 1 | 1170 | 1178 | 11 | 3 | 1 | 306 | 317 | −11 | 7 | 1 | 663 | 727 | −6 | 10 | 1 | 187 | 167 |
| −17 | 1 | 1 | 696 | 695 | 13 | 3 | 1 | 210 | 220 | −9 | 7 | 1 | 550 | 562 | −4 | 10 | 1 | 1017 | 1044 |
| −15 | 1 | 1 | 515 | 525 | 15 | 3 | 1 | 448 | 444 | −2 | 10 | 1 | 1554 | 1571 | 8 | 0 | 2 | 3478 | 3537 |
| −13 | 1 | 1 | 1186 | 1211 | 17 | 3 | 1 | 232 | 246 | 0 | 10 | 1 | 1399 | 1407 | 10 | 0 | 2 | 1197 | 1186 |
| −11 | 1 | 1 | 3331 | 3248 | 19 | 3 | 1 | 305 | 288 | 2 | 10 | 1 | 1325 | 1328 | 12 | 0 | 2 | 858 | 872 |
| −9 | 1 | 1 | 3748 | 3860 | 21 | 3 | 1 | 442 | 428 | 6 | 10 | 1 | 1119 | 1107 | 14 | 0 | 2 | 617 | 614 |
| −7 | 1 | 1 | 706 | 706 | 25 | 3 | 1 | 160 | 128 | 8 | 10 | 1 | 999 | 1005 | 16 | 0 | 2 | 1730 | 1681 |
| −5 | 1 | 1 | 465 | 472 | −22 | 4 | 1 | 266 | 275 | 10 | 10 | 1 | 1316 | 1312 | 18 | 0 | 2 | 1023 | 1011 |
| −3 | 1 | 1 | 3777 | 3637 | −20 | 4 | 1 | 569 | 598 | 12 | 10 | 1 | 723 | 740 | 20 | 0 | 2 | 374 | 366 |
| −1 | 1 | 1 | 5915 | 5903 | −18 | 4 | 1 | 675 | 677 | 14 | 10 | 1 | 276 | 258 | 22 | 0 | 2 | 271 | 297 |
| 1 | 1 | 1 | 2840 | 2847 | −14 | 4 | 1 | 434 | 436 | 16 | 10 | 1 | 449 | 441 | 24 | 0 | 2 | 446 | 448 |
| 3 | 1 | 1 | 1779 | 1770 | −12 | 4 | 1 | 1238 | 1250 | 18 | 10 | 1 | 548 | 549 | 26 | 0 | 2 | 725 | 724 |
| 7 | 1 | 1 | 2125 | 2096 | −10 | 4 | 1 | 1678 | 1694 | −11 | 11 | 1 | 251 | 281 | −25 | 1 | 2 | 267 | 280 |
| 9 | 1 | 1 | 2700 | 2710 | −8 | 4 | 1 | 1310 | 1254 | −9 | 11 | 1 | 414 | 441 | −19 | 1 | 2 | 312 | 296 |
| 11 | 1 | 1 | 1511 | 1547 | −6 | 4 | 1 | 204 | 236 | −7 | 11 | 1 | 307 | 299 | −17 | 1 | 2 | 675 | 672 |
| 13 | 1 | 1 | 939 | 974 | −4 | 4 | 1 | 2233 | 2150 | −1 | 11 | 1 | 352 | 378 | −15 | 1 | 2 | 607 | 590 |
| 15 | 1 | 1 | 487 | 497 | −2 | 4 | 1 | 3028 | 3001 | 1 | 11 | 1 | 517 | 503 | −11 | 1 | 2 | 191 | 133 |
| 17 | 1 | 1 | 963 | 953 | 0 | 4 | 1 | 2891 | 2844 | 3 | 11 | 1 | 456 | 466 | −9 | 1 | 2 | 1751 | 1795 |
| 19 | 1 | 1 | 958 | 934 | 2 | 4 | 1 | 612 | 591 | 5 | 11 | 1 | 203 | 194 | −7 | 1 | 2 | 987 | 1033 |
| 21 | 1 | 1 | 574 | 576 | 4 | 4 | 1 | 1443 | 1429 | 9 | 11 | 1 | 200 | 236 | −5 | 1 | 2 | 553 | 555 |
| 23 | 1 | 1 | 616 | 585 | 6 | 4 | 1 | 1894 | 1888 | 11 | 11 | 1 | 497 | 510 | −3 | 1 | 2 | 1603 | 1623 |
| −22 | 2 | 1 | 467 | 475 | 8 | 4 | 1 | 2844 | 2821 | 13 | 11 | 1 | 509 | 499 | −1 | 1 | 2 | 398 | 390 |
| −18 | 2 | 1 | 241 | 272 | 10 | 4 | 1 | 1548 | 1543 | 15 | 11 | 1 | 187 | 208 | 1 | 1 | 2 | 814 | 777 |
| −14 | 2 | 1 | 487 | 519 | 14 | 4 | 1 | 368 | 360 | −12 | 12 | 1 | 774 | 752 | 3 | 1 | 2 | 2183 | 2185 |
| −12 | 2 | 1 | 674 | 663 | 16 | 4 | 1 | 1436 | 1410 | −10 | 12 | 1 | 381 | 373 | 5 | 1 | 2 | 434 | 429 |
| 18 | 4 | 1 | 1198 | 1175 | −7 | 7 | 1 | 659 | 674 | −8 | 12 | 1 | 236 | 236 | 7 | 1 | 2 | 1374 | 1382 |
| 20 | 4 | 1 | 873 | 860 | −5 | 7 | 1 | 583 | 576 | −4 | 12 | 1 | 419 | 425 | 9 | 1 | 2 | 895 | 900 |
| 22 | 4 | 1 | 358 | 361 | −3 | 7 | 1 | 1042 | 1052 | −2 | 12 | 1 | 485 | 499 | 11 | 1 | 2 | 537 | 562 |
| 24 | 4 | 1 | 284 | 250 | −1 | 7 | 1 | 1219 | 1194 | 0 | 12 | 1 | 622 | 630 | 13 | 1 | 2 | 285 | 292 |
| −25 | 5 | 1 | 349 | 351 | 1 | 7 | 1 | 1211 | 1194 | 2 | 12 | 1 | 885 | 890 | 15 | 1 | 2 | 647 | 649 |
| −23 | 5 | 1 | 262 | 252 | 3 | 7 | 1 | 659 | 661 | 4 | 12 | 1 | 437 | 445 | 17 | 1 | 2 | 1746 | 1711 |
| −21 | 5 | 1 | 392 | 383 | 5 | 7 | 1 | 530 | 517 | 8 | 12 | 1 | 251 | 274 | 19 | 1 | 2 | 685 | 685 |
| −19 | 5 | 1 | 933 | 954 | 7 | 7 | 1 | 804 | 780 | 10 | 12 | 1 | 772 | 763 | 21 | 1 | 2 | 638 | 625 |
| −17 | 5 | 1 | 458 | 471 | 9 | 7 | 1 | 1433 | 1392 | 12 | 12 | 1 | 721 | 725 | 25 | 1 | 2 | 748 | 709 |
| −13 | 5 | 1 | 1029 | 1032 | 11 | 7 | 1 | 1079 | 1061 | −9 | 13 | 1 | 263 | 288 | −26 | 2 | 2 | 279 | 301 |
| −11 | 5 | 1 | 2675 | 2685 | 13 | 7 | 1 | 523 | 529 | −5 | 13 | 1 | 279 | 313 | −24 | 2 | 2 | 373 | 380 |
| −9 | 5 | 1 | 3071 | 3038 | 15 | 7 | 1 | 241 | 251 | −3 | 13 | 1 | 680 | 707 | −22 | 2 | 2 | 311 | 306 |
| −7 | 5 | 1 | 698 | 718 | 17 | 7 | 1 | 618 | 599 | −1 | 13 | 1 | 425 | 441 | −20 | 2 | 2 | 282 | 280 |
| −5 | 5 | 1 | 440 | 460 | 19 | 7 | 1 | 825 | 793 | 1 | 13 | 1 | 436 | 428 | −16 | 2 | 2 | 365 | 364 |
| −3 | 5 | 1 | 2203 | 2228 | 21 | 7 | 1 | 869 | 836 | 5 | 13 | 1 | 704 | 711 | −14 | 2 | 2 | 896 | 881 |
| −1 | 5 | 1 | 3894 | 3899 | 23 | 7 | 1 | 201 | 211 | 7 | 13 | 1 | 782 | 782 | −12 | 2 | 2 | 753 | 762 |
| 1 | 5 | 1 | 2799 | 2787 | −22 | 8 | 1 | 404 | 441 | 9 | 13 | 1 | 556 | 571 | −10 | 2 | 2 | 760 | 713 |
| 3 | 5 | 1 | 443 | 452 | −18 | 8 | 1 | 331 | 349 | −26 | 0 | 2 | 434 | 421 | −8 | 2 | 2 | 152 | 108 |
| 5 | 5 | 1 | 533 | 513 | −16 | 8 | 1 | 476 | 500 | −24 | 0 | 2 | 817 | 822 | −4 | 2 | 2 | 1313 | 1356 |
| 7 | 5 | 1 | 1367 | 1332 | −14 | 8 | 1 | 479 | 531 | −22 | 0 | 2 | 1096 | 1107 | −2 | 2 | 2 | 1413 | 1419 |
| 9 | 5 | 1 | 1937 | 1932 | −10 | 8 | 1 | 617 | 610 | −20 | 0 | 2 | 1591 | 1569 | 0 | 2 | 2 | 1573 | 1560 |
| 11 | 5 | 1 | 920 | 911 | −8 | 8 | 1 | 346 | 336 | −18 | 0 | 2 | 592 | 595 | 2 | 2 | 2 | 1180 | 1176 |
| 13 | 5 | 1 | 1336 | 1312 | −6 | 8 | 1 | 186 | 184 | −16 | 0 | 2 | 1418 | 1397 | 4 | 2 | 2 | 494 | 467 |
| 15 | 5 | 1 | 658 | 660 | −4 | 8 | 1 | 368 | 373 | −14 | 0 | 2 | 1816 | 1784 | 6 | 2 | 2 | 450 | 466 |
| 17 | 5 | 1 | 706 | 688 | −2 | 8 | 1 | 457 | 444 | −12 | 0 | 2 | 4108 | 4013 | 8 | 2 | 2 | 823 | 831 |
| 19 | 5 | 1 | 609 | 588 | 0 | 8 | 1 | 524 | 514 | −10 | 0 | 2 | 2924 | 2818 | 10 | 2 | 2 | 863 | 864 |
| 21 | 5 | 1 | 514 | 506 | 2 | 8 | 1 | 552 | 553 | −8 | 0 | 2 | 353 | 381 | 12 | 2 | 2 | 866 | 871 |
| 23 | 5 | 1 | 571 | 541 | 4 | 8 | 1 | 936 | 943 | −6 | 0 | 2 | 2451 | 2405 | 14 | 2 | 2 | 145 | 125 |
| −24 | 6 | 1 | 406 | 423 | 6 | 8 | 1 | 468 | 486 | −4 | 0 | 2 | 3143 | 3043 | 16 | 2 | 2 | 494 | 484 |
| −22 | 6 | 1 | 710 | 741 | 8 | 8 | 1 | 901 | 884 | −2 | 0 | 2 | 4371 | 4488 | 18 | 2 | 2 | 778 | 759 |
| −20 | 6 | 1 | 504 | 528 | 12 | 8 | 1 | 325 | 305 | 0 | 0 | 2 | 2190 | 2190 | 20 | 2 | 2 | 516 | 503 |
| −18 | 6 | 1 | 177 | 177 | 14 | 8 | 1 | 285 | 271 | 2 | 0 | 2 | 2088 | 2068 | 22 | 2 | 2 | 163 | 175 |
| −14 | 6 | 1 | 992 | 1032 | 16 | 8 | 1 | 743 | 718 | 6 | 0 | 2 | 1789 | 1769 | 24 | 2 | 2 | 228 | 211 |
| −12 | 6 | 1 | 1412 | 1521 | 18 | 8 | 1 | 597 | 508 | 26 | 2 | 2 | 367 | 333 | −1 | 5 | 2 | 2346 | 2353 |
| −10 | 6 | 1 | 1189 | 1170 | 20 | 8 | 1 | 184 | 162 | −25 | 3 | 2 | 277 | 297 | 1 | 5 | 2 | 655 | 661 |
| −8 | 6 | 1 | 1064 | 1108 | −15 | 9 | 1 | 203 | 205 | −17 | 3 | 2 | 1061 | 1079 | 3 | 5 | 2 | 653 | 648 |
| −6 | 6 | 1 | 211 | 232 | −13 | 9 | 1 | 513 | 541 | −15 | 3 | 2 | 860 | 876 | 5 | 5 | 2 | 1455 | 1442 |
| −4 | 6 | 1 | 1519 | 1517 | −7 | 9 | 1 | 346 | 331 | −13 | 3 | 2 | 435 | 426 | 7 | 5 | 2 | 1493 | 1475 |
| −2 | 6 | 1 | 1516 | 1516 | −5 | 9 | 1 | 593 | 593 | −11 | 3 | 2 | 299 | 276 | 9 | 5 | 2 | 1106 | 1105 |
| 0 | 6 | 1 | 1527 | 1482 | −3 | 9 | 1 | 834 | 827 | −9 | 3 | 2 | 1479 | 1375 | 11 | 5 | 2 | 561 | 560 |
| 2 | 6 | 1 | 2328 | 2331 | 3 | 9 | 1 | 191 | 172 | −7 | 3 | 2 | 2320 | 2464 | 13 | 5 | 2 | 604 | 595 |
| 6 | 6 | 1 | 981 | 956 | 5 | 9 | 1 | 1430 | 1420 | −5 | 3 | 2 | 1495 | 1466 | 15 | 5 | 2 | 1004 | 900 |
| 8 | 6 | 1 | 625 | 617 | 7 | 9 | 1 | 939 | 917 | −3 | 3 | 2 | 558 | 570 | 17 | 5 | 2 | 452 | 437 |
| 10 | 6 | 1 | 1291 | 1252 | 9 | 9 | 1 | 417 | 379 | −1 | 3 | 2 | 137 | 148 | 19 | 5 | 2 | 693 | 602 |

TABLE 1-continued

MO2CO2S4(CO)2(NCCH3)2[S2CH(C2H5)2]2

| H | K | L | FOBS | FCAL | H | K | L | FOBS | FCAL | H | K | L | FOBS | FCAL | H | K | L | FOBS | FCAL |
|---|---|---|------|------|---|---|---|------|------|---|---|---|------|------|---|---|---|------|------|
| 1 | 3 | 2 | 1268 | 1225 | 23 | 5 | 2 | 331 | 333 | 11 | 9 | 2 | 420 | 409 | −13 | 1 | 3 | 943 | 904 |
| 3 | 3 | 2 | 288 | 314 | −24 | 6 | 2 | 467 | 463 | 13 | 9 | 2 | 395 | 373 | −11 | 1 | 3 | 723 | 699 |
| 5 | 3 | 2 | 900 | 903 | −22 | 6 | 2 | 439 | 430 | 15 | 9 | 2 | 733 | 716 | −9 | 1 | 3 | 353 | 341 |
| 7 | 3 | 2 | 2724 | 2737 | −20 | 6 | 2 | 478 | 489 | 17 | 9 | 2 | 820 | 793 | −7 | 1 | 3 | 237 | 287 |
| 9 | 3 | 2 | 1623 | 1622 | −16 | 6 | 2 | 580 | 609 | 19 | 9 | 2 | 582 | 578 | −5 | 1 | 3 | 747 | 682 |
| 11 | 3 | 2 | 441 | 464 | −14 | 6 | 2 | 760 | 819 | −14 | 10 | 2 | 254 | 248 | −3 | 1 | 3 | 671 | 710 |
| 13 | 3 | 2 | 297 | 284 | −12 | 6 | 2 | 831 | 896 | −10 | 10 | 2 | 264 | 239 | −1 | 1 | 3 | 1082 | 1117 |
| 15 | 3 | 2 | 1551 | 1502 | −10 | 6 | 2 | 1085 | 1119 | −8 | 10 | 2 | 194 | 223 | 1 | 1 | 3 | 543 | 529 |
| 17 | 3 | 2 | 2237 | 2182 | −8 | 6 | 2 | 154 | 108 | −6 | 10 | 2 | 584 | 618 | 3 | 1 | 3 | 1887 | 1846 |
| 19 | 3 | 2 | 1362 | 1324 | −6 | 6 | 2 | 222 | 189 | −4 | 10 | 2 | 1085 | 1096 | 5 | 1 | 3 | 134 | 143 |
| 21 | 3 | 2 | 656 | 641 | −4 | 6 | 2 | 509 | 511 | −2 | 10 | 2 | 371 | 334 | 7 | 1 | 3 | 1258 | 1261 |
| 25 | 3 | 2 | 1024 | 980 | −2 | 6 | 2 | 946 | 953 | 0 | 10 | 2 | 176 | 151 | 9 | 1 | 3 | 373 | 367 |
| −24 | 4 | 2 | 226 | 235 | 0 | 6 | 2 | 1542 | 1527 | 2 | 10 | 2 | 751 | 756 | 11 | 1 | 3 | 409 | 404 |
| −22 | 4 | 2 | 378 | 371 | 2 | 6 | 2 | 706 | 703 | 4 | 10 | 2 | 1594 | 1595 | 13 | 1 | 3 | 1038 | 1049 |
| −20 | 4 | 2 | 850 | 876 | 4 | 6 | 2 | 1466 | 1466 | 6 | 10 | 2 | 1032 | 1032 | 17 | 1 | 3 | 439 | 441 |
| −18 | 4 | 2 | 605 | 623 | 6 | 6 | 2 | 541 | 523 | 8 | 10 | 2 | 230 | 240 | 23 | 1 | 3 | 393 | 391 |
| −16 | 4 | 2 | 243 | 212 | 8 | 6 | 2 | 1252 | 1221 | 10 | 10 | 2 | 252 | 251 | 25 | 1 | 3 | 444 | 426 |
| −14 | 4 | 2 | 445 | 419 | 10 | 6 | 2 | 1233 | 1211 | 12 | 10 | 2 | 864 | 850 | −26 | 2 | 3 | 724 | 696 |
| −12 | 4 | 2 | 1578 | 1551 | 12 | 6 | 2 | 1506 | 1480 | 14 | 10 | 2 | 900 | 876 | −24 | 2 | 3 | 149 | 187 |
| −10 | 4 | 2 | 1672 | 1643 | 14 | 6 | 2 | 251 | 280 | 16 | 10 | 2 | 333 | 348 | −22 | 2 | 3 | 370 | 387 |
| −8 | 4 | 2 | 423 | 418 | 16 | 6 | 2 | 606 | 573 | −15 | 11 | 2 | 546 | 509 | −20 | 2 | 3 | 829 | 822 |
| −6 | 4 | 2 | 753 | 751 | 18 | 6 | 2 | 1043 | 1028 | −13 | 11 | 2 | 799 | 778 | −18 | 2 | 3 | 1804 | 1859 |
| −2 | 4 | 2 | 2151 | 2127 | 20 | 6 | 2 | 786 | 759 | −16 | 2 | 3 | 1418 | 1403 | 10 | 4 | 3 | 567 | 570 |
| 0 | 4 | 2 | 564 | 560 | 22 | 6 | 2 | 323 | 316 | −14 | 2 | 3 | 195 | 202 | 12 | 4 | 3 | 782 | 779 |
| 2 | 4 | 2 | 858 | 826 | −23 | 7 | 2 | 370 | 381 | −12 | 2 | 3 | 1050 | 1008 | 14 | 4 | 3 | 1446 | 1425 |
| 4 | 4 | 2 | 1584 | 1554 | −21 | 7 | 2 | 328 | 331 | −10 | 2 | 3 | 2267 | 2126 | 16 | 4 | 3 | 1572 | 1556 |
| 6 | 4 | 2 | 774 | 766 | −17 | 7 | 2 | 346 | 353 | −8 | 2 | 3 | 2458 | 2356 | 18 | 4 | 3 | 931 | 931 |
| 8 | 4 | 2 | 529 | 523 | −13 | 7 | 2 | 352 | 360 | −6 | 2 | 3 | 595 | 631 | 22 | 4 | 3 | 219 | 202 |
| 10 | 4 | 2 | 261 | 265 | −11 | 7 | 2 | 435 | 447 | −2 | 2 | 3 | 324 | 323 | 24 | 4 | 3 | 654 | 616 |
| 12 | 4 | 2 | 865 | 863 | −9 | 7 | 2 | 1014 | 1042 | 0 | 2 | 3 | 803 | 797 | −25 | 5 | 3 | 610 | 616 |
| 14 | 4 | 2 | 1066 | 1029 | −7 | 7 | 2 | 1403 | 1444 | 2 | 2 | 3 | 101 | 107 | −23 | 5 | 3 | 422 | 428 |
| 16 | 4 | 2 | 241 | 239 | −3 | 7 | 2 | 216 | 234 | 4 | 2 | 3 | 140 | 162 | −21 | 5 | 3 | 558 | 502 |
| 20 | 4 | 2 | 179 | 168 | −1 | 7 | 2 | 273 | 280 | 6 | 2 | 3 | 2646 | 2666 | −19 | 5 | 3 | 197 | 155 |
| 22 | 4 | 2 | 322 | 298 | 1 | 7 | 2 | 1849 | 1856 | 8 | 2 | 3 | 2329 | 2354 | −17 | 5 | 3 | 777 | 829 |
| −25 | 5 | 2 | 338 | 347 | 3 | 7 | 2 | 448 | 447 | 10 | 2 | 3 | 834 | 853 | −15 | 5 | 3 | 457 | 481 |
| −23 | 5 | 2 | 573 | 571 | 5 | 7 | 2 | 225 | 196 | 12 | 2 | 3 | 704 | 709 | −13 | 5 | 3 | 171 | 160 |
| −21 | 5 | 2 | 514 | 526 | 7 | 7 | 2 | 661 | 658 | 14 | 2 | 3 | 1288 | 1274 | −11 | 5 | 3 | 486 | 492 |
| −19 | 5 | 2 | 297 | 301 | 11 | 7 | 2 | 238 | 229 | 16 | 2 | 3 | 2250 | 2213 | −9 | 5 | 3 | 165 | 178 |
| −15 | 5 | 2 | 763 | 780 | 13 | 7 | 2 | 156 | 134 | 18 | 2 | 3 | 1159 | 1125 | −7 | 5 | 3 | 419 | 447 |
| −13 | 5 | 2 | 1611 | 1586 | 15 | 7 | 2 | 674 | 664 | 20 | 2 | 3 | 889 | 880 | −5 | 5 | 3 | 712 | 723 |
| −11 | 5 | 2 | 1126 | 1121 | 17 | 7 | 2 | 781 | 758 | 22 | 2 | 3 | 143 | 132 | −3 | 5 | 3 | 283 | 275 |
| −9 | 5 | 2 | 956 | 936 | 19 | 7 | 2 | 440 | 398 | 24 | 2 | 3 | 777 | 741 | −1 | 5 | 3 | 165 | 131 |
| −7 | 5 | 2 | 216 | 207 | 21 | 7 | 2 | 173 | 132 | −21 | 3 | 3 | 370 | 351 | 1 | 5 | 3 | 606 | 608 |
| −5 | 5 | 2 | 1635 | 1694 | −22 | 8 | 2 | 171 | 168 | −19 | 3 | 3 | 524 | 541 | 3 | 5 | 3 | 1573 | 1584 |
| −3 | 5 | 2 | 1705 | 1749 | −20 | 8 | 2 | 268 | 255 | −17 | 3 | 3 | 193 | 148 | 5 | 5 | 3 | 398 | 410 |
| −18 | 8 | 2 | 369 | 385 | −11 | 11 | 2 | 620 | 618 | −15 | 3 | 3 | 291 | 285 | 7 | 5 | 3 | 438 | 431 |
| −16 | 8 | 2 | 408 | 423 | −9 | 11 | 2 | 510 | 494 | −13 | 3 | 3 | 341 | 330 | 9 | 5 | 3 | 169 | 169 |
| −14 | 8 | 2 | 477 | 519 | −7 | 11 | 2 | 297 | 304 | −11 | 3 | 3 | 395 | 390 | 11 | 5 | 3 | 367 | 358 |
| −12 | 8 | 2 | 263 | 239 | −5 | 11 | 2 | 514 | 535 | −9 | 3 | 3 | 166 | 140 | 13 | 5 | 3 | 411 | 388 |
| −10 | 8 | 2 | 486 | 467 | −3 | 11 | 2 | 676 | 699 | −7 | 3 | 3 | 660 | 643 | 15 | 5 | 3 | 367 | 330 |
| −8 | 8 | 2 | 249 | 213 | −1 | 11 | 2 | 715 | 732 | −5 | 3 | 3 | 754 | 755 | 17 | 5 | 3 | 323 | 284 |
| −6 | 8 | 2 | 954 | 925 | 1 | 11 | 2 | 1112 | 1124 | −3 | 3 | 3 | 982 | 939 | 19 | 5 | 3 | 257 | 244 |
| −4 | 8 | 2 | 945 | 930 | 3 | 11 | 2 | 258 | 276 | 3 | 3 | 3 | 941 | 941 | 23 | 5 | 3 | 238 | 219 |
| −2 | 8 | 2 | 379 | 374 | 5 | 11 | 2 | 411 | 416 | 5 | 3 | 3 | 1319 | 1307 | −24 | 6 | 3 | 386 | 394 |
| 0 | 8 | 2 | 490 | 493 | 7 | 11 | 2 | 356 | 354 | 7 | 3 | 3 | 319 | 343 | −22 | 6 | 3 | 594 | 608 |
| 4 | 8 | 2 | 1350 | 1324 | 9 | 11 | 2 | 762 | 783 | 9 | 3 | 3 | 944 | 935 | −20 | 6 | 3 | 251 | 252 |
| 6 | 8 | 2 | 1093 | 1073 | 11 | 11 | 2 | 538 | 554 | 13 | 3 | 3 | 663 | 654 | −18 | 6 | 3 | 343 | 352 |
| 8 | 8 | 2 | 1065 | 1056 | 13 | 11 | 2 | 151 | 73 | 17 | 3 | 3 | 779 | 769 | −16 | 6 | 3 | 176 | 217 |
| 10 | 8 | 2 | 1017 | 1025 | −4 | 12 | 2 | 221 | 262 | 19 | 3 | 3 | 593 | 591 | −14 | 6 | 3 | 906 | 970 |
| 12 | 8 | 2 | 179 | 148 | 0 | 12 | 2 | 212 | 243 | 25 | 3 | 3 | 224 | 229 | −12 | 6 | 3 | 674 | 734 |
| 14 | 8 | 2 | 812 | 811 | 2 | 12 | 2 | 191 | 212 | −26 | 4 | 3 | 664 | 657 | −10 | 6 | 3 | 1084 | 1113 |
| 16 | 8 | 2 | 783 | 784 | 4 | 12 | 2 | 274 | 270 | −24 | 4 | 3 | 560 | 555 | −8 | 6 | 3 | 503 | 541 |
| 18 | 8 | 2 | 831 | 826 | 6 | 12 | 2 | 178 | 155 | −22 | 4 | 3 | 249 | 237 | −6 | 6 | 3 | 854 | 870 |
| 20 | 8 | 2 | 741 | 710 | 8 | 12 | 2 | 330 | 340 | −20 | 4 | 3 | 320 | 352 | −4 | 6 | 3 | 1210 | 1212 |
| −21 | 9 | 2 | 272 | 277 | 10 | 12 | 2 | 577 | 582 | −18 | 4 | 3 | 1169 | 1216 | −2 | 6 | 3 | 601 | 610 |
| −17 | 9 | 2 | 219 | 211 | 12 | 12 | 2 | 180 | 170 | −16 | 4 | 3 | 1515 | 1588 | 0 | 6 | 3 | 334 | 335 |
| −15 | 9 | 2 | 552 | 598 | −9 | 13 | 2 | 248 | 226 | −14 | 4 | 3 | 1252 | 1273 | 2 | 6 | 3 | 700 | 680 |
| −13 | 9 | 2 | 671 | 683 | −5 | 13 | 2 | 283 | 272 | −12 | 4 | 3 | 459 | 467 | 4 | 6 | 3 | 857 | 849 |
| −11 | 9 | 2 | 681 | 650 | −3 | 13 | 2 | 439 | 460 | −10 | 4 | 3 | 1066 | 1048 | 6 | 6 | 3 | 484 | 486 |
| −9 | 9 | 2 | 227 | 232 | −1 | 13 | 2 | 422 | 408 | −8 | 4 | 3 | 2465 | 2499 | 8 | 6 | 3 | 312 | 209 |
| −7 | 9 | 2 | 509 | 506 | 1 | 13 | 2 | 199 | 205 | −6 | 4 | 3 | 2067 | 2172 | 10 | 6 | 3 | 956 | 939 |
| −5 | 9 | 2 | 1138 | 1150 | 5 | 13 | 2 | 183 | 233 | −4 | 4 | 3 | 1435 | 1484 | 16 | 6 | 3 | 520 | 522 |
| −3 | 9 | 2 | 1134 | 1146 | 7 | 13 | 2 | 218 | 243 | −2 | 4 | 3 | 1332 | 1311 | 18 | 6 | 3 | 176 | 139 |
| −1 | 9 | 2 | 827 | 832 | −27 | 1 | 3 | 436 | 451 | 0 | 4 | 3 | 1023 | 1009 | 20 | 6 | 3 | 316 | 275 |
| 1 | 9 | 2 | 255 | 242 | −25 | 1 | 3 | 783 | 770 | 2 | 4 | 3 | 928 | 949 | 22 | 6 | 3 | 355 | 354 |
| 3 | 9 | 2 | 724 | 702 | −23 | 1 | 3 | 654 | 644 | 4 | 4 | 3 | 2318 | 2358 | −23 | 7 | 3 | 245 | 274 |
| 5 | 9 | 2 | 913 | 926 | −21 | 1 | 3 | 626 | 622 | 6 | 4 | 3 | 2262 | 2294 | −21 | 7 | 3 | 173 | 186 |
| 7 | 9 | 2 | 1121 | 1109 | −17 | 1 | 3 | 1004 | 1061 | 8 | 4 | 3 | 1473 | 1477 | −19 | 7 | 3 | 546 | 575 |
| 9 | 9 | 2 | 782 | 771 | −15 | 1 | 3 | 951 | 961 | −17 | 7 | 3 | 655 | 706 | 19 | 9 | 3 | 462 | 452 |

TABLE 1-continued

MO2CO2S4(CO)2(NCCH3)2[S2CH(C2H5)2]2

| H | K | L | FOBS | FCAL | H | K | L | FOBS | FCAL | H | K | L | FOBS | FCAL |
|---|---|---|------|------|---|---|---|------|------|---|---|---|------|------|
| −15 | 7 | 3 | 628 | 655 | −18 | 10 | 3 | 280 | 306 | −5 | 1 | 4 | 1002 | 994 | 17 | 3 | 4 | 567 | 580 |
| −13 | 7 | 3 | 334 | 354 | −16 | 10 | 3 | 568 | 603 | −3 | 1 | 4 | 556 | 555 | 19 | 3 | 4 | 316 | 313 |
| −11 | 7 | 3 | 385 | 405 | −14 | 10 | 3 | 910 | 906 | −1 | 1 | 4 | 903 | 884 | 23 | 3 | 4 | 422 | 420 |
| −9 | 7 | 3 | 672 | 650 | −12 | 10 | 3 | 517 | 506 | 1 | 1 | 4 | 849 | 814 | −26 | 4 | 4 | 365 | 376 |
| −7 | 7 | 3 | 966 | 976 | −8 | 10 | 3 | 402 | 406 | 3 | 1 | 4 | 960 | 936 | −22 | 4 | 4 | 351 | 353 |
| −5 | 7 | 3 | 191 | 161 | −6 | 10 | 3 | 907 | 909 | 5 | 1 | 4 | 3286 | 3229 | −20 | 4 | 4 | 162 | 143 |
| −3 | 7 | 3 | 364 | 373 | −4 | 10 | 3 | 751 | 762 | 7 | 1 | 4 | 1171 | 1207 | −18 | 4 | 4 | 409 | 422 |
| −1 | 7 | 3 | 201 | 185 | −2 | 10 | 3 | 477 | 495 | 9 | 1 | 4 | 171 | 176 | −16 | 4 | 4 | 246 | 251 |
| 1 | 7 | 3 | 176 | 195 | 0 | 10 | 3 | 307 | 301 | 11 | 1 | 4 | 219 | 200 | −14 | 4 | 4 | 389 | 357 |
| 3 | 7 | 3 | 243 | 194 | 2 | 10 | 3 | 441 | 442 | 13 | 1 | 4 | 807 | 816 | −12 | 4 | 4 | 265 | 235 |
| 5 | 7 | 3 | 670 | 668 | 4 | 10 | 3 | 757 | 775 | 15 | 1 | 4 | 1096 | 1083 | −10 | 4 | 4 | 159 | 121 |
| 7 | 7 | 3 | 753 | 751 | 6 | 10 | 3 | 528 | 511 | 17 | 1 | 4 | 447 | 442 | −8 | 4 | 4 | 207 | 196 |
| 9 | 7 | 3 | 1097 | 1103 | 8 | 10 | 3 | 503 | 517 | 19 | 1 | 4 | 347 | 344 | −6 | 4 | 4 | 1067 | 1113 |
| 11 | 7 | 3 | 448 | 432 | 12 | 10 | 3 | 392 | 393 | 23 | 1 | 4 | 241 | 236 | −4 | 4 | 4 | 674 | 663 |
| 13 | 7 | 3 | 428 | 398 | 14 | 10 | 3 | 517 | 514 | 25 | 1 | 4 | 301 | 311 | −2 | 4 | 4 | 204 | 206 |
| 15 | 7 | 3 | 705 | 687 | 16 | 10 | 3 | 358 | 367 | −26 | 2 | 4 | 361 | 370 | 0 | 4 | 4 | 415 | 410 |
| 17 | 7 | 3 | 961 | 938 | −13 | 11 | 3 | 329 | 304 | −24 | 2 | 4 | 241 | 229 | 2 | 4 | 4 | 317 | 318 |
| 19 | 7 | 3 | 670 | 648 | −11 | 11 | 3 | 323 | 280 | −20 | 2 | 4 | 490 | 504 | 4 | 4 | 4 | 345 | 348 |
| −20 | 8 | 3 | 278 | 297 | −7 | 11 | 3 | 369 | 344 | −18 | 2 | 4 | 665 | 693 | 6 | 4 | 4 | 124 | 154 |
| −18 | 8 | 3 | 734 | 780 | −5 | 11 | 3 | 675 | 671 | −16 | 2 | 4 | 517 | 536 | 8 | 4 | 4 | 1695 | 1706 |
| −16 | 8 | 3 | 683 | 726 | −3 | 11 | 3 | 427 | 436 | −10 | 2 | 4 | 1005 | 942 | 10 | 4 | 4 | 1052 | 1086 |
| −12 | 8 | 3 | 307 | 291 | 1 | 11 | 3 | 395 | 401 | −8 | 2 | 4 | 608 | 582 | 12 | 4 | 4 | 185 | 151 |
| −10 | 8 | 3 | 733 | 713 | 3 | 11 | 3 | 733 | 741 | −6 | 2 | 4 | 444 | 450 | 16 | 4 | 4 | 827 | 808 |
| −8 | 8 | 3 | 1142 | 1086 | 5 | 11 | 3 | 549 | 551 | −4 | 2 | 4 | 370 | 363 | 18 | 4 | 4 | 1036 | 1004 |
| −6 | 8 | 3 | 493 | 476 | 9 | 11 | 3 | 313 | 327 | −2 | 2 | 4 | 315 | 294 | 20 | 4 | 4 | 359 | 356 |
| −4 | 8 | 3 | 400 | 399 | 11 | 11 | 3 | 425 | 416 | 2 | 2 | 4 | 746 | 736 | −25 | 5 | 4 | 539 | 527 |
| −2 | 8 | 3 | 270 | 257 | 13 | 11 | 3 | 327 | 305 | 4 | 2 | 4 | 924 | 933 | −23 | 5 | 4 | 457 | 475 |
| 0 | 8 | 3 | 477 | 479 | −12 | 12 | 3 | 352 | 338 | 6 | 2 | 4 | 616 | 649 | −19 | 5 | 4 | 495 | 504 |
| 2 | 8 | 3 | 393 | 400 | −10 | 12 | 3 | 365 | 363 | 8 | 2 | 4 | 252 | 265 | −17 | 5 | 4 | 902 | 944 |
| 4 | 8 | 3 | 442 | 436 | −8 | 12 | 3 | 402 | 396 | 10 | 2 | 4 | 671 | 659 | −15 | 5 | 4 | 1028 | 1106 |
| 6 | 8 | 3 | 1097 | 1097 | −6 | 12 | 3 | 223 | 241 | 12 | 2 | 4 | 547 | 534 | −13 | 5 | 4 | 467 | 501 |
| 8 | 8 | 3 | 637 | 626 | −4 | 12 | 3 | 386 | 402 | 14 | 2 | 4 | 388 | 383 | −11 | 5 | 4 | 251 | 197 |
| 10 | 8 | 3 | 274 | 265 | −2 | 12 | 3 | 287 | 290 | −9 | 5 | 4 | 1155 | 1175 | −20 | 8 | 4 | 564 | 592 |
| 12 | 8 | 3 | 217 | 223 | 0 | 12 | 3 | 429 | 415 | −7 | 5 | 4 | 1582 | 1654 | −18 | 8 | 4 | 672 | 715 |
| 14 | 8 | 3 | 454 | 451 | 4 | 12 | 3 | 277 | 264 | −5 | 5 | 4 | 1485 | 1518 | −16 | 8 | 4 | 805 | 845 |
| 16 | 8 | 3 | 784 | 767 | −9 | 13 | 3 | 486 | 477 | −3 | 5 | 4 | 275 | 262 | −14 | 8 | 4 | 548 | 588 |
| 18 | 8 | 3 | 428 | 419 | −7 | 13 | 3 | 754 | 791 | −1 | 5 | 4 | 756 | 769 | −12 | 8 | 4 | 274 | 295 |
| −19 | 9 | 3 | 396 | 428 | −5 | 13 | 3 | 1027 | 1041 | 1 | 5 | 4 | 1040 | 1061 | −10 | 8 | 4 | 639 | 631 |
| −17 | 9 | 3 | 469 | 511 | −3 | 13 | 3 | 460 | 474 | 3 | 5 | 4 | 2138 | 2161 | −8 | 8 | 4 | 1300 | 1260 |
| −15 | 9 | 3 | 844 | 902 | 1 | 13 | 3 | 373 | 377 | 5 | 5 | 4 | 653 | 633 | −6 | 8 | 4 | 1614 | 1577 |
| −13 | 9 | 3 | 578 | 562 | 3 | 13 | 3 | 1004 | 1018 | 7 | 5 | 4 | 216 | 199 | −4 | 8 | 4 | 1078 | 1048 |
| −9 | 9 | 3 | 551 | 523 | 5 | 13 | 3 | 894 | 913 | 9 | 5 | 4 | 753 | 781 | −2 | 8 | 4 | 134 | 59 |
| −7 | 9 | 3 | 1508 | 1471 | 7 | 13 | 3 | 560 | 579 | 11 | 5 | 4 | 1237 | 1196 | 0 | 8 | 4 | 291 | 290 |
| −5 | 9 | 3 | 2289 | 2238 | −26 | 0 | 4 | 1011 | 1014 | 13 | 5 | 4 | 718 | 710 | 2 | 8 | 4 | 1247 | 1232 |
| −3 | 9 | 3 | 1079 | 1073 | −24 | 0 | 4 | 501 | 487 | 15 | 5 | 4 | 401 | 383 | 4 | 8 | 4 | 1430 | 1423 |
| −1 | 9 | 3 | 249 | 246 | −22 | 0 | 4 | 199 | 208 | 19 | 5 | 4 | 349 | 333 | 6 | 8 | 4 | 946 | 944 |
| 1 | 9 | 3 | 996 | 1002 | −20 | 0 | 4 | 362 | 359 | 21 | 5 | 4 | 392 | 363 | 8 | 8 | 4 | 905 | 899 |
| 3 | 9 | 3 | 2211 | 2186 | −18 | 0 | 4 | 1578 | 1665 | 23 | 5 | 4 | 300 | 309 | 10 | 8 | 4 | 159 | 60 |
| 5 | 9 | 3 | 1847 | 1850 | −16 | 0 | 4 | 837 | 831 | −24 | 6 | 4 | 234 | 243 | 12 | 8 | 4 | 639 | 625 |
| 7 | 9 | 3 | 983 | 966 | −14 | 0 | 4 | 526 | 503 | −20 | 6 | 4 | 545 | 570 | 14 | 8 | 4 | 815 | 804 |
| 9 | 9 | 3 | 353 | 327 | −12 | 0 | 4 | 244 | 191 | −18 | 6 | 4 | 683 | 715 | 16 | 8 | 4 | 808 | 808 |
| 11 | 9 | 3 | 641 | 646 | −10 | 0 | 4 | 1393 | 1314 | −16 | 6 | 4 | 429 | 472 | 18 | 8 | 4 | 778 | 754 |
| 13 | 9 | 3 | 1146 | 1118 | −8 | 0 | 4 | 2112 | 1974 | −14 | 6 | 4 | 188 | 210 | −19 | 9 | 4 | 637 | 698 |
| 15 | 9 | 3 | 721 | 723 | −6 | 0 | 4 | 287 | 285 | −12 | 6 | 4 | 191 | 178 | −17 | 9 | 4 | 899 | 958 |
| 17 | 9 | 3 | 595 | 589 | −4 | 0 | 4 | 1728 | 1677 | −10 | 6 | 4 | 840 | 873 | −15 | 9 | 4 | 728 | 782 |
| −2 | 0 | 4 | 1710 | 1730 | 16 | 0 | 4 | 336 | 365 | −8 | 6 | 4 | 289 | 295 | −13 | 9 | 4 | 235 | 242 |
| 0 | 0 | 4 | 3242 | 3238 | 18 | 0 | 4 | 207 | 203 | −4 | 6 | 4 | 176 | 131 | −11 | 9 | 4 | 564 | 555 |
| 2 | 0 | 4 | 2649 | 2604 | 22 | 0 | 4 | 271 | 273 | 0 | 6 | 4 | 586 | 589 | −9 | 9 | 4 | 1310 | 1260 |
| 4 | 0 | 4 | 1046 | 1052 | 24 | 0 | 4 | 233 | 244 | 2 | 6 | 4 | 487 | 484 | −7 | 9 | 4 | 1143 | 1113 |
| 6 | 0 | 4 | 311 | 297 | −25 | 3 | 4 | 570 | 550 | 4 | 6 | 4 | 454 | 446 | −5 | 9 | 4 | 1011 | 992 |
| 8 | 0 | 4 | 1879 | 1874 | −23 | 3 | 4 | 240 | 223 | 6 | 6 | 4 | 478 | 467 | −3 | 9 | 4 | 289 | 309 |
| 10 | 0 | 4 | 2235 | 2295 | −21 | 3 | 4 | 782 | 796 | 8 | 6 | 4 | 168 | 119 | −1 | 9 | 4 | 537 | 516 |
| 12 | 0 | 4 | 1325 | 1341 | −19 | 3 | 4 | 1786 | 1827 | 10 | 6 | 4 | 706 | 701 | 1 | 9 | 4 | 1152 | 1148 |
| 14 | 0 | 4 | 1326 | 1345 | −17 | 3 | 4 | 1763 | 1855 | 12 | 6 | 4 | 569 | 552 | 3 | 9 | 4 | 1159 | 1170 |
| 16 | 0 | 4 | 554 | 565 | −15 | 3 | 4 | 684 | 660 | 14 | 6 | 4 | 594 | 574 | 5 | 9 | 4 | 940 | 935 |
| 18 | 0 | 4 | 1028 | 1038 | −11 | 3 | 4 | 1314 | 1275 | 16 | 6 | 4 | 392 | 376 | 9 | 9 | 4 | 458 | 446 |
| 20 | 0 | 4 | 886 | 879 | −9 | 3 | 4 | 2478 | 2459 | 18 | 6 | 4 | 302 | 315 | 11 | 9 | 4 | 773 | 777 |
| 22 | 0 | 4 | 482 | 491 | −7 | 3 | 4 | 1847 | 1906 | 22 | 6 | 4 | 367 | 344 | 13 | 9 | 4 | 527 | 535 |
| 24 | 0 | 4 | 426 | 419 | −5 | 3 | 4 | 1948 | 2045 | −23 | 7 | 4 | 242 | 234 | 15 | 9 | 4 | 285 | 276 |
| −27 | 1 | 4 | 654 | 644 | −3 | 3 | 4 | 2037 | 2003 | −21 | 7 | 4 | 350 | 371 | −16 | 10 | 4 | 610 | 608 |
| −25 | 1 | 4 | 214 | 235 | −1 | 3 | 4 | 400 | 405 | −19 | 7 | 4 | 863 | 907 | −14 | 10 | 4 | 728 | 713 |
| −23 | 1 | 4 | 239 | 232 | 1 | 3 | 4 | 1837 | 1802 | −17 | 7 | 4 | 648 | 701 | −10 | 10 | 4 | 267 | 236 |
| −21 | 1 | 4 | 571 | 570 | 3 | 3 | 4 | 2064 | 2121 | −13 | 7 | 4 | 306 | 312 | −8 | 10 | 4 | 820 | 810 |
| −19 | 1 | 4 | 1249 | 1277 | 5 | 3 | 4 | 2581 | 2600 | −11 | 7 | 4 | 531 | 466 | −6 | 10 | 4 | 1391 | 1367 |
| −17 | 1 | 4 | 1156 | 1214 | 7 | 3 | 4 | 2173 | 2211 | −9 | 7 | 4 | 1086 | 1044 | −4 | 10 | 4 | 732 | 725 |
| −13 | 1 | 4 | 241 | 258 | 9 | 3 | 4 | 248 | 108 | −7 | 7 | 4 | 628 | 641 | −2 | 10 | 4 | 221 | 248 |
| −11 | 1 | 4 | 823 | 779 | 11 | 3 | 4 | 388 | 387 | −5 | 7 | 4 | 355 | 348 | 0 | 10 | 4 | 188 | 174 |
| −9 | 1 | 4 | 1926 | 1835 | 13 | 3 | 4 | 1358 | 1363 | −3 | 7 | 4 | 797 | 796 | 2 | 10 | 4 | 1043 | 1045 |
| −7 | 1 | 4 | 1006 | 1024 | 15 | 3 | 4 | 1596 | 1596 | −1 | 7 | 4 | 276 | 282 | 4 | 10 | 4 | 917 | 932 |

TABLE 1-continued

MO2CO2S4(CO)2(NCCH3)2[S2CH(C2H5)2]2

| H | K | L | FOBS | FCAL | H | K | L | FOBS | FCAL | H | K | L | FOBS | FCAL | H | K | L | FOBS | FCAL |
|---|---|---|------|------|---|---|---|------|------|---|---|---|------|------|---|---|---|------|------|
| 1 | 7 | 4 | 339 | 323 | 6 | 10 | 4 | 565 | 561 | −8 | 6 | 5 | 196 | 217 | −9 | 9 | 5 | 1026 | 986 |
| 3 | 7 | 4 | 643 | 647 | 8 | 10 | 4 | 358 | 338 | −4 | 6 | 5 | 1538 | 1591 | −7 | 9 | 5 | 1554 | 1503 |
| 5 | 7 | 4 | 1011 | 1018 | 12 | 10 | 4 | 432 | 450 | −2 | 6 | 5 | 908 | 927 | −5 | 9 | 5 | 561 | 549 |
| 7 | 7 | 4 | 924 | 924 | 14 | 10 | 4 | 312 | 299 | 0 | 6 | 5 | 734 | 745 | −3 | 9 | 5 | 224 | 170 |
| 11 | 7 | 4 | 169 | 167 | 16 | 10 | 4 | 324 | 298 | 2 | 6 | 5 | 587 | 589 | 1 | 9 | 5 | 778 | 781 |
| 13 | 7 | 4 | 239 | 212 | −15 | 11 | 4 | 419 | 426 | 4 | 6 | 5 | 341 | 372 | 3 | 9 | 5 | 1102 | 1076 |
| 15 | 7 | 4 | 539 | 518 | −7 | 11 | 4 | 474 | 471 | 6 | 6 | 5 | 936 | 947 | 5 | 9 | 5 | 709 | 696 |
| 21 | 7 | 4 | 412 | 380 | −5 | 11 | 4 | 319 | 321 | 8 | 6 | 5 | 635 | 626 | 7 | 9 | 5 | 659 | 643 |
| −22 | 8 | 4 | 222 | 253 | −3 | 11 | 4 | 254 | 243 | 10 | 6 | 5 | 981 | 969 | 9 | 9 | 5 | 306 | 297 |
| −1 | 11 | 4 | 198 | 199 | 12 | 2 | 5 | 592 | 593 | 12 | 6 | 5 | 667 | 654 | 11 | 9 | 5 | 607 | 606 |
| 1 | 11 | 4 | 354 | 347 | 14 | 2 | 5 | 845 | 816 | 16 | 6 | 5 | 168 | 169 | 13 | 9 | 5 | 535 | 513 |
| 3 | 11 | 4 | 379 | 384 | 16 | 2 | 5 | 412 | 425 | 18 | 6 | 5 | 437 | 439 | 15 | 9 | 5 | 488 | 476 |
| 7 | 11 | 4 | 145 | 132 | 18 | 2 | 5 | 239 | 231 | 20 | 6 | 5 | 640 | 621 | 17 | 9 | 5 | 407 | 401 |
| 11 | 11 | 4 | 317 | 337 | 20 | 2 | 5 | 405 | 389 | 22 | 6 | 5 | 298 | 296 | −18 | 10 | 5 | 491 | 509 |
| 13 | 11 | 4 | 387 | 382 | 24 | 2 | 5 | 332 | 329 | −23 | 7 | 5 | 256 | 268 | −16 | 10 | 5 | 630 | 654 |
| −12 | 12 | 4 | 285 | 280 | −23 | 3 | 5 | 235 | 206 | −21 | 7 | 5 | 491 | 524 | −12 | 10 | 5 | 569 | 559 |
| −10 | 12 | 4 | 411 | 424 | −21 | 3 | 5 | 363 | 359 | −19 | 7 | 5 | 689 | 713 | −10 | 10 | 5 | 740 | 715 |
| −8 | 12 | 4 | 377 | 403 | −17 | 3 | 5 | 468 | 499 | −17 | 7 | 5 | 489 | 499 | −8 | 10 | 5 | 1078 | 1057 |
| −6 | 12 | 4 | 336 | 343 | −15 | 3 | 5 | 361 | 373 | −15 | 7 | 5 | 260 | 243 | −6 | 10 | 5 | 915 | 901 |
| 0 | 12 | 4 | 157 | 146 | −13 | 3 | 5 | 228 | 197 | −13 | 7 | 5 | 284 | 288 | −4 | 10 | 5 | 216 | 233 |
| 2 | 12 | 4 | 342 | 356 | −11 | 3 | 5 | 460 | 420 | −11 | 7 | 5 | 648 | 656 | −2 | 10 | 5 | 898 | 901 |
| 4 | 12 | 4 | 361 | 357 | −9 | 3 | 5 | 250 | 241 | −9 | 7 | 5 | 924 | 873 | 0 | 10 | 5 | 1174 | 1179 |
| 6 | 12 | 4 | 255 | 282 | −7 | 3 | 5 | 487 | 518 | −7 | 7 | 5 | 1244 | 1174 | 2 | 10 | 5 | 1215 | 1219 |
| 3 | 13 | 4 | 239 | 241 | −5 | 3 | 5 | 663 | 660 | −5 | 7 | 5 | 829 | 849 | 4 | 10 | 5 | 469 | 467 |
| −27 | 1 | 5 | 458 | 443 | −3 | 3 | 5 | 299 | 309 | −3 | 7 | 5 | 297 | 324 | 6 | 10 | 5 | 347 | 334 |
| −23 | 1 | 5 | 145 | 66 | −1 | 3 | 5 | 1054 | 1068 | −1 | 7 | 5 | 826 | 820 | 8 | 10 | 5 | 717 | 720 |
| −21 | 1 | 5 | 163 | 180 | 1 | 3 | 5 | 158 | 159 | 1 | 7 | 5 | 1240 | 1242 | 10 | 10 | 5 | 934 | 944 |
| −19 | 1 | 5 | 839 | 843 | 3 | 3 | 5 | 579 | 586 | 3 | 7 | 5 | 1159 | 1173 | 12 | 10 | 5 | 756 | 744 |
| −17 | 1 | 5 | 341 | 357 | 5 | 3 | 5 | 972 | 969 | 5 | 7 | 5 | 614 | 609 | 14 | 10 | 5 | 193 | 209 |
| −13 | 1 | 5 | 178 | 163 | 7 | 3 | 5 | 1186 | 1206 | 9 | 7 | 5 | 657 | 640 | −11 | 11 | 5 | 243 | 212 |
| −11 | 1 | 5 | 919 | 880 | 9 | 3 | 5 | 660 | 690 | 11 | 7 | 5 | 740 | 704 | −3 | 11 | 5 | 196 | 189 |
| −9 | 1 | 5 | 1814 | 1734 | 13 | 3 | 5 | 560 | 562 | 13 | 7 | 5 | 767 | 752 | −1 | 11 | 5 | 330 | 333 |
| −7 | 1 | 5 | 1547 | 1517 | 15 | 3 | 5 | 693 | 685 | 15 | 7 | 5 | 453 | 446 | 1 | 11 | 5 | 228 | 243 |
| −5 | 1 | 5 | 527 | 554 | 17 | 3 | 5 | 520 | 498 | 17 | 7 | 5 | 195 | 164 | 3 | 11 | 5 | 142 | 194 |
| −3 | 1 | 5 | 419 | 396 | 19 | 3 | 5 | 154 | 146 | 19 | 7 | 5 | 201 | 214 | 7 | 11 | 5 | 303 | 304 |
| −1 | 1 | 5 | 3525 | 3398 | 21 | 3 | 5 | 296 | 283 | −20 | 8 | 5 | 383 | 389 | 9 | 11 | 5 | 370 | 356 |
| 1 | 1 | 5 | 3236 | 3142 | −26 | 4 | 5 | 543 | 544 | −18 | 8 | 5 | 755 | 808 | 11 | 11 | 5 | 176 | 186 |
| 3 | 1 | 5 | 1492 | 1488 | −22 | 4 | 5 | 375 | 379 | −16 | 8 | 5 | 613 | 643 | −12 | 12 | 5 | 373 | 364 |
| 5 | 1 | 5 | 296 | 300 | −20 | 4 | 5 | 986 | 1015 | −14 | 8 | 5 | 705 | 731 | −8 | 12 | 5 | 163 | 148 |
| 7 | 1 | 5 | 2297 | 2323 | −18 | 4 | 5 | 1429 | 1508 | −12 | 8 | 5 | 196 | 161 | −6 | 12 | 5 | 200 | 186 |
| 9 | 1 | 5 | 2544 | 2617 | −16 | 4 | 5 | 937 | 989 | −10 | 8 | 5 | 1089 | 1061 | −4 | 12 | 5 | 401 | 399 |
| 11 | 1 | 5 | 1554 | 1575 | −14 | 4 | 5 | 653 | 671 | −8 | 8 | 5 | 1104 | 1058 | −2 | 12 | 5 | 224 | 201 |
| 13 | 1 | 5 | 766 | 761 | −12 | 4 | 5 | 413 | 421 | 0 | 12 | 5 | 187 | 171 | −16 | 2 | 6 | 153 | 145 |
| 15 | 1 | 5 | 332 | 313 | −10 | 4 | 5 | 1771 | 1790 | 2 | 12 | 5 | 317 | 330 | −12 | 2 | 6 | 900 | 871 |
| 17 | 1 | 5 | 910 | 913 | −8 | 4 | 5 | 2645 | 2713 | 10 | 12 | 5 | 419 | 404 | −10 | 2 | 6 | 1028 | 1025 |
| 19 | 1 | 5 | 700 | 691 | −6 | 4 | 5 | 2404 | 2468 | −7 | 13 | 5 | 1063 | 1074 | −8 | 2 | 6 | 871 | 859 |
| 21 | 1 | 5 | 439 | 419 | −4 | 4 | 5 | 1272 | 1300 | −5 | 13 | 5 | 518 | 518 | −6 | 2 | 6 | 553 | 534 |
| 23 | 1 | 5 | 446 | 458 | −2 | 4 | 5 | 1264 | 1274 | −1 | 13 | 5 | 436 | 458 | −4 | 2 | 6 | 557 | 551 |
| −26 | 2 | 5 | 245 | 239 | 0 | 4 | 5 | 2838 | 2911 | 1 | 13 | 5 | 803 | 801 | −2 | 2 | 6 | 1821 | 1856 |
| −24 | 2 | 5 | 233 | 241 | 2 | 4 | 5 | 2500 | 2535 | 3 | 13 | 5 | 770 | 783 | 0 | 2 | 6 | 1414 | 1459 |
| −22 | 2 | 5 | 221 | 201 | 4 | 4 | 5 | 1859 | 1911 | −26 | 0 | 6 | 168 | 159 | 2 | 2 | 6 | 696 | 714 |
| −20 | 2 | 5 | 1045 | 1053 | 6 | 4 | 5 | 369 | 360 | −22 | 0 | 6 | 259 | 264 | 4 | 2 | 6 | 205 | 201 |
| −18 | 2 | 5 | 1178 | 1191 | 8 | 4 | 5 | 1328 | 1349 | −20 | 0 | 6 | 1055 | 1068 | 6 | 2 | 6 | 559 | 583 |
| −16 | 2 | 5 | 628 | 645 | 10 | 4 | 5 | 1213 | 1244 | −18 | 0 | 6 | 651 | 649 | 8 | 2 | 6 | 729 | 767 |
| −14 | 2 | 5 | 885 | 860 | 12 | 4 | 5 | 1001 | 975 | −14 | 0 | 6 | 481 | 480 | 10 | 2 | 6 | 1059 | 1096 |
| −12 | 2 | 5 | 323 | 314 | 14 | 4 | 5 | 603 | 591 | −12 | 0 | 6 | 1858 | 1781 | 12 | 2 | 6 | 672 | 669 |
| −10 | 2 | 5 | 1435 | 1424 | 18 | 4 | 5 | 226 | 195 | −10 | 0 | 6 | 4346 | 4129 | 14 | 2 | 6 | 409 | 399 |
| −8 | 2 | 5 | 2004 | 1967 | 20 | 4 | 5 | 254 | 242 | −8 | 0 | 6 | 1990 | 1879 | 16 | 2 | 6 | 285 | 265 |
| −6 | 2 | 5 | 2069 | 2103 | 22 | 4 | 5 | 315 | 326 | −6 | 0 | 6 | 226 | 153 | 18 | 2 | 6 | 366 | 359 |
| −4 | 2 | 5 | 2840 | 2720 | −19 | 5 | 5 | 329 | 364 | −4 | 0 | 6 | 1950 | 1962 | 20 | 2 | 6 | 532 | 525 |
| −2 | 2 | 5 | 1091 | 1031 | −15 | 5 | 5 | 261 | 277 | −2 | 0 | 6 | 6397 | 6139 | 22 | 2 | 6 | 394 | 382 |
| 0 | 2 | 5 | 1759 | 1725 | −11 | 5 | 5 | 854 | 892 | 0 | 0 | 6 | 4640 | 4799 | −23 | 3 | 6 | 149 | 150 |
| 2 | 2 | 5 | 1698 | 1729 | −9 | 5 | 5 | 1115 | 1162 | 2 | 0 | 6 | 2292 | 2342 | −21 | 3 | 6 | 523 | 533 |
| 4 | 2 | 5 | 2610 | 2654 | −3 | 5 | 5 | 753 | 771 | 4 | 0 | 6 | 392 | 406 | −19 | 3 | 6 | 1146 | 1181 |
| 6 | 2 | 5 | 1645 | 1695 | −1 | 5 | 5 | 2333 | 2366 | 6 | 0 | 6 | 3260 | 3334 | −17 | 3 | 6 | 939 | 974 |
| 1 | 5 | 5 | 1869 | 1902 | −6 | 8 | 5 | 1322 | 1299 | 8 | 0 | 6 | 4099 | 4236 | −15 | 3 | 6 | 1144 | 1207 |
| 3 | 5 | 5 | 611 | 595 | −4 | 8 | 5 | 1082 | 1060 | 10 | 0 | 6 | 2108 | 2128 | −13 | 3 | 6 | 760 | 762 |
| 7 | 5 | 5 | 2012 | 2032 | 0 | 8 | 5 | 1018 | 1018 | 12 | 0 | 6 | 1057 | 1071 | −11 | 3 | 6 | 1444 | 1455 |
| 9 | 5 | 5 | 2045 | 2065 | 2 | 8 | 5 | 1002 | 979 | 16 | 0 | 6 | 1002 | 1001 | −9 | 3 | 6 | 2482 | 2526 |
| 11 | 5 | 5 | 1073 | 1074 | 4 | 8 | 5 | 979 | 977 | 18 | 0 | 6 | 1154 | 1142 | −7 | 3 | 6 | 1843 | 1928 |
| 13 | 5 | 5 | 466 | 440 | 6 | 8 | 5 | 233 | 232 | 20 | 0 | 6 | 714 | 704 | −5 | 3 | 6 | 2160 | 2210 |
| 15 | 5 | 5 | 351 | 354 | 8 | 8 | 5 | 435 | 432 | 22 | 0 | 6 | 890 | 877 | −3 | 3 | 6 | 339 | 352 |
| 17 | 5 | 5 | 1009 | 991 | 10 | 8 | 5 | 308 | 326 | 24 | 0 | 6 | 174 | 154 | −1 | 3 | 6 | 1821 | 1868 |
| 19 | 5 | 5 | 471 | 438 | 16 | 8 | 5 | 212 | 262 | −21 | 1 | 6 | 214 | 225 | 1 | 3 | 6 | 1703 | 1736 |
| 21 | 5 | 5 | 348 | 336 | 9 | 5 | 5 | 594 | 609 | −19 | 1 | 6 | 545 | 531 | 3 | 3 | 6 | 1697 | 1729 |
| −24 | 6 | 5 | 252 | 236 | −17 | 9 | 5 | 897 | 946 | −17 | 1 | 6 | 622 | 654 | 5 | 3 | 6 | 607 | 619 |
| −16 | 6 | 5 | 484 | 505 | −15 | 9 | 5 | 844 | 854 | −15 | 1 | 6 | 711 | 696 | 7 | 3 | 6 | 794 | 801 |
| −12 | 6 | 5 | 897 | 898 | −13 | 9 | 5 | 348 | 293 | −13 | 1 | 6 | 660 | 634 | 9 | 3 | 6 | 678 | 663 |
| −10 | 6 | 5 | 541 | 566 | −11 | 9 | 5 | 803 | 775 | −11 | 1 | 6 | 932 | 903 | 11 | 3 | 6 | 301 | 279 |

TABLE 1-continued

MO2CO2S4(CO)2(NCCH3)2[S2CH(C2H5)2]2

| H | K | L | FOBS | FCAL | H | K | L | FOBS | FCAL | H | K | L | FOBS | FCAL |
|---|---|---|------|------|---|---|---|------|------|---|---|---|------|------|
| −9 | 1 | 6 | 1305 | 1314 | 13 | 3 | 6 | 539 | 538 | 11 | 11 | 6 | 960 | 957 | 
| −7 | 1 | 6 | 1188 | 1178 | 17 | 3 | 6 | 248 | 244 | −10 | 12 | 6 | 381 | 394 |
| −5 | 1 | 6 | 1548 | 1549 | 21 | 3 | 6 | 358 | 350 | −8 | 12 | 6 | 674 | 683 |
| −3 | 1 | 6 | 250 | 235 | 23 | 3 | 6 | 321 | 331 | −6 | 12 | 6 | 458 | 454 |
| −1 | 1 | 6 | 1990 | 2006 | −22 | 4 | 6 | 285 | 201 | −2 | 12 | 6 | 257 | 287 |
| 3 | 1 | 6 | 879 | 904 | −12 | 4 | 6 | 715 | 716 | 0 | 12 | 6 | 475 | 473 |
| 5 | 1 | 6 | 525 | 552 | −10 | 4 | 6 | 1609 | 1648 | 2 | 12 | 6 | 567 | 578 |
| 7 | 1 | 6 | 178 | 203 | −8 | 4 | 6 | 231 | 272 | 4 | 12 | 6 | 243 | 256 |
| 9 | 1 | 6 | 223 | 243 | −4 | 4 | 6 | 958 | 994 | −3 | 13 | 6 | 206 | 213 |
| 11 | 1 | 6 | 175 | 154 | −2 | 4 | 6 | 3027 | 3066 | −1 | 13 | 6 | 214 | 150 |
| 13 | 1 | 6 | 485 | 471 | 0 | 4 | 6 | 2054 | 2118 | 1 | 13 | 6 | 212 | 216 |
| 15 | 1 | 6 | 220 | 227 | 4 | 4 | 6 | 591 | 594 | −25 | 1 | 7 | 164 | 152 |
| 17 | 1 | 6 | 212 | 180 | 6 | 4 | 6 | 1629 | 1663 | −23 | 1 | 7 | 229 | 214 |
| 21 | 1 | 6 | 297 | 294 | 8 | 4 | 6 | 1830 | 1873 | −21 | 1 | 7 | 773 | 778 |
| 23 | 1 | 6 | 212 | 179 | 10 | 4 | 6 | 747 | 747 | −19 | 1 | 7 | 721 | 755 |
| −24 | 2 | 6 | 164 | 124 | 16 | 4 | 6 | 669 | 652 | −15 | 1 | 7 | 287 | 299 |
| −22 | 2 | 6 | 177 | 175 | 18 | 4 | 6 | 398 | 390 | −13 | 1 | 7 | 1836 | 1753 |
| −20 | 2 | 6 | 287 | 293 | 22 | 4 | 6 | 316 | 305 | −11 | 1 | 7 | 2904 | 2833 |
| −18 | 2 | 6 | 423 | 412 | −23 | 5 | 6 | 245 | 261 | −9 | 1 | 7 | 1092 | 1089 |
| −21 | 5 | 6 | 488 | 487 | 11 | 7 | 6 | 709 | 713 | −7 | 1 | 7 | 302 | 253 |
| −19 | 5 | 6 | 604 | 644 | 13 | 7 | 6 | 224 | 205 | −5 | 1 | 7 | 1076 | 1114 |
| −17 | 5 | 6 | 695 | 728 | 15 | 7 | 6 | 193 | 177 | −3 | 1 | 7 | 3429 | 3499 |
| −15 | 5 | 6 | 198 | 184 | 19 | 7 | 6 | 400 | 383 | −1 | 1 | 7 | 2714 | 2789 |
| −13 | 5 | 6 | 951 | 999 | −20 | 8 | 6 | 396 | 426 | 1 | 1 | 7 | 1565 | 1642 |
| −11 | 5 | 6 | 1261 | 1283 | −18 | 8 | 6 | 553 | 588 | 3 | 1 | 7 | 679 | 703 |
| −9 | 5 | 6 | 1355 | 1423 | −16 | 8 | 6 | 683 | 685 | 5 | 1 | 7 | 724 | 730 |
| −7 | 5 | 6 | 1132 | 1157 | −14 | 8 | 6 | 307 | 292 | 7 | 1 | 7 | 2078 | 2115 |
| −5 | 5 | 6 | 329 | 336 | −12 | 8 | 6 | 353 | 364 | 9 | 1 | 7 | 1697 | 1723 |
| −3 | 5 | 6 | 1642 | 1671 | −10 | 8 | 6 | 563 | 545 | 11 | 1 | 7 | 1464 | 1464 |
| −1 | 5 | 6 | 1763 | 1802 | −8 | 8 | 6 | 1161 | 1114 | 13 | 1 | 7 | 1006 | 1024 |
| 1 | 5 | 6 | 1946 | 1959 | −6 | 8 | 6 | 828 | 798 | 15 | 1 | 7 | 337 | 335 |
| 3 | 5 | 6 | 619 | 604 | −4 | 8 | 6 | 278 | 272 | 17 | 1 | 7 | 852 | 857 |
| 5 | 5 | 6 | 585 | 567 | 0 | 8 | 6 | 686 | 683 | 19 | 1 | 7 | 870 | 877 |
| 7 | 5 | 6 | 1158 | 1171 | 2 | 8 | 6 | 1366 | 1346 | 21 | 1 | 7 | 905 | 893 |
| 9 | 5 | 6 | 1337 | 1338 | 4 | 8 | 6 | 682 | 679 | 23 | 1 | 7 | 321 | 316 |
| 11 | 5 | 6 | 1171 | 1158 | 6 | 8 | 6 | 464 | 440 | −24 | 2 | 7 | 407 | 391 |
| 13 | 5 | 6 | 302 | 301 | 10 | 8 | 6 | 716 | 727 | −20 | 2 | 7 | 614 | 611 |
| 15 | 5 | 6 | 269 | 271 | 12 | 8 | 6 | 791 | 791 | −18 | 2 | 7 | 494 | 511 |
| 17 | 5 | 6 | 478 | 489 | 14 | 8 | 6 | 317 | 319 | −16 | 2 | 7 | 729 | 751 |
| 19 | 5 | 6 | 639 | 631 | 16 | 8 | 6 | 171 | 156 | −14 | 2 | 7 | 1208 | 1282 |
| 21 | 5 | 6 | 406 | 399 | 18 | 8 | 6 | 330 | 322 | −12 | 2 | 7 | 690 | 685 |
| −24 | 6 | 6 | 192 | 140 | −19 | 9 | 6 | 522 | 549 | −10 | 2 | 7 | 771 | 768 |
| −20 | 6 | 6 | 446 | 475 | −17 | 9 | 6 | 695 | 707 | −8 | 2 | 7 | 407 | 415 |
| −18 | 6 | 6 | 326 | 336 | −15 | 9 | 6 | 458 | 444 | −6 | 2 | 7 | 1821 | 1824 |
| −14 | 6 | 6 | 176 | 128 | −13 | 9 | 6 | 319 | 267 | −4 | 2 | 7 | 307 | 326 |
| −12 | 6 | 6 | 967 | 971 | −11 | 9 | 6 | 907 | 883 | −2 | 2 | 7 | 341 | 336 |
| −10 | 6 | 6 | 1438 | 1419 | −9 | 9 | 6 | 1309 | 1263 | 0 | 2 | 7 | 362 | 354 |
| −8 | 6 | 6 | 1313 | 1355 | −7 | 9 | 6 | 1238 | 1206 | 2 | 2 | 7 | 461 | 444 |
| −6 | 6 | 6 | 609 | 622 | −3 | 9 | 6 | 919 | 899 | 4 | 2 | 7 | 1229 | 1223 |
| −4 | 6 | 6 | 808 | 805 | −1 | 9 | 6 | 1391 | 1386 | 6 | 2 | 7 | 214 | 207 |
| −2 | 6 | 6 | 2133 | 2161 | 1 | 9 | 6 | 1101 | 1119 | 10 | 2 | 7 | 155 | 94 |
| 0 | 6 | 6 | 2171 | 2178 | 3 | 9 | 6 | 508 | 498 | 12 | 2 | 7 | 870 | 868 |
| 2 | 6 | 6 | 1475 | 1503 | 5 | 9 | 6 | 373 | 376 | 7 | 5 | 7 | 1494 | 1491 |
| 4 | 6 | 6 | 481 | 478 | 7 | 9 | 6 | 860 | 848 | 9 | 5 | 7 | 1159 | 1141 |
| 6 | 6 | 6 | 1052 | 1051 | 9 | 9 | 6 | 764 | 760 | 11 | 5 | 7 | 1176 | 1178 |
| 8 | 6 | 6 | 1630 | 1612 | 11 | 9 | 6 | 478 | 478 | 13 | 5 | 7 | 1095 | 1087 |
| 10 | 6 | 6 | 1414 | 1395 | 13 | 9 | 6 | 168 | 157 | 15 | 5 | 7 | 149 | 135 |
| 12 | 6 | 6 | 1020 | 1005 | 15 | 9 | 6 | 266 | 247 | 17 | 5 | 7 | 569 | 562 |
| 14 | 6 | 6 | 538 | 526 | −18 | 10 | 6 | 416 | 411 | 19 | 5 | 7 | 757 | 749 |
| 16 | 6 | 6 | 387 | 397 | −16 | 10 | 6 | 220 | 251 | 21 | 5 | 7 | 825 | 807 |
| 18 | 6 | 6 | 561 | 548 | −8 | 10 | 6 | 294 | 278 | −22 | 6 | 7 | 443 | 451 |
| 20 | 6 | 6 | 792 | 769 | −6 | 10 | 6 | 151 | 146 | −16 | 6 | 7 | 692 | 730 |
| −23 | 7 | 6 | 366 | 364 | −4 | 10 | 6 | 184 | 177 | −14 | 6 | 7 | 1044 | 1074 |
| −19 | 7 | 6 | 425 | 460 | −2 | 10 | 6 | 473 | 472 | −12 | 6 | 7 | 555 | 530 |
| −17 | 7 | 6 | 336 | 319 | 0 | 10 | 6 | 266 | 276 | −10 | 6 | 7 | 547 | 544 |
| −15 | 7 | 6 | 932 | 963 | 6 | 10 | 6 | 356 | 337 | −8 | 6 | 7 | 619 | 587 |
| −13 | 7 | 6 | 776 | 791 | 8 | 10 | 6 | 510 | 512 | −6 | 6 | 7 | 1104 | 1122 |
| −11 | 7 | 6 | 371 | 370 | −15 | 11 | 6 | 364 | 382 | −4 | 6 | 7 | 1354 | 1396 |
| −9 | 7 | 6 | 557 | 536 | −13 | 11 | 6 | 711 | 699 | −2 | 6 | 7 | 1077 | 1073 |
| −7 | 7 | 6 | 683 | 649 | −11 | 11 | 6 | 425 | 382 | 0 | 6 | 7 | 1294 | 1316 |
| −5 | 7 | 6 | 1366 | 1318 | −9 | 11 | 6 | 447 | 445 | 2 | 6 | 7 | 403 | 383 |
| −3 | 7 | 6 | 300 | 286 | −5 | 11 | 6 | 443 | 442 | 4 | 6 | 7 | 894 | 893 |
| −1 | 7 | 6 | 206 | 207 | −3 | 11 | 6 | 627 | 629 | 6 | 6 | 7 | 820 | 811 |
| 5 | 7 | 6 | 416 | 404 | −1 | 11 | 6 | 648 | 661 | 8 | 6 | 7 | 961 | 955 |
| 9 | 7 | 6 | 501 | 474 | 1 | 11 | 6 | 933 | 936 | 10 | 6 | 7 | 1288 | 1281 |
| 3 | 11 | 6 | 544 | 552 | 14 | 2 | 7 | 459 | 483 | 12 | 6 | 7 | 926 | 933 |
| 5 | 11 | 6 | 235 | 221 | 16 | 2 | 7 | 539 | 519 | 14 | 6 | 7 | 236 | 236 |
| 7 | 11 | 6 | 376 | 385 | 18 | 2 | 7 | 480 | 471 | 16 | 6 | 7 | 157 | 143 |
| 9 | 11 | 6 | 897 | 897 | 20 | 2 | 7 | 689 | 679 | 18 | 6 | 7 | 352 | 353 |
|  |  |  |  |  |  |  |  |  |  | 20 | 6 | 7 | 186 | 243 |

TABLE 1-continued
MO2CO2S4(CO)2(NCCH3)2[S2CH(C2H5)2]2

| H | K | L | FOBS | FCAL | H | K | L | FOBS | FCAL | H | K | L | FOBS | FCAL | H | K | L | FOBS | FCAL |
|---|---|---|------|------|---|---|---|------|------|---|---|---|------|------|---|---|---|------|------|
| −21 | 7 | 7 | 239 | 280 | 12 | 10 | 7 | 393 | 402 | 16 | 2 | 8 | 410 | 404 | 3 | 5 | 8 | 563 | 559 |
| −19 | 7 | 7 | 259 | 256 | −9 | 11 | 7 | 314 | 319 | 18 | 2 | 8 | 600 | 599 | 5 | 5 | 8 | 1218 | 1211 |
| −17 | 7 | 7 | 308 | 311 | −7 | 11 | 7 | 211 | 243 | 20 | 2 | 8 | 427 | 430 | 7 | 5 | 8 | 835 | 816 |
| −15 | 7 | 7 | 295 | 277 | −3 | 11 | 7 | 252 | 249 | −23 | 3 | 8 | 164 | 190 | 9 | 5 | 8 | 920 | 909 |
| −13 | 7 | 7 | 572 | 560 | −1 | 11 | 7 | 258 | 271 | −21 | 3 | 8 | 396 | 411 | 11 | 5 | 8 | 164 | 158 |
| −11 | 7 | 7 | 570 | 587 | 1 | 11 | 7 | 445 | 464 | −19 | 3 | 8 | 163 | 191 | 13 | 5 | 8 | 403 | 415 |
| −9 | 7 | 7 | 798 | 752 | 3 | 11 | 7 | 450 | 464 | 15 | 5 | 8 | 288 | 285 | −11 | 9 | 8 | 187 | 201 |
| −7 | 7 | 7 | 432 | 406 | 9 | 11 | 7 | 362 | 368 | 17 | 5 | 8 | 542 | 543 | −7 | 9 | 8 | 452 | 449 |
| −3 | 7 | 7 | 353 | 354 | −10 | 12 | 7 | 354 | 343 | 19 | 5 | 8 | 336 | 339 | −5 | 9 | 8 | 499 | 490 |
| −1 | 7 | 7 | 1039 | 1002 | −8 | 12 | 7 | 255 | 221 | −22 | 6 | 8 | 449 | 466 | −3 | 9 | 8 | 462 | 467 |
| 1 | 7 | 7 | 1311 | 1294 | −6 | 12 | 7 | 269 | 240 | −20 | 6 | 8 | 184 | 186 | −1 | 9 | 8 | 299 | 299 |
| 3 | 7 | 7 | 739 | 724 | −4 | 12 | 7 | 534 | 537 | −18 | 6 | 8 | 255 | 253 | 1 | 9 | 8 | 145 | 141 |
| 7 | 7 | 7 | 687 | 673 | −2 | 12 | 7 | 575 | 586 | −16 | 6 | 8 | 637 | 619 | 3 | 9 | 8 | 352 | 329 |
| 9 | 7 | 7 | 1054 | 1041 | 0 | 12 | 7 | 946 | 936 | −14 | 6 | 8 | 927 | 926 | 5 | 9 | 8 | 476 | 487 |
| 11 | 7 | 7 | 1271 | 1271 | 2 | 12 | 7 | 490 | 529 | −12 | 6 | 8 | 868 | 871 | 7 | 9 | 8 | 418 | 406 |
| 13 | 7 | 7 | 454 | 468 | 6 | 12 | 7 | 286 | 290 | −10 | 6 | 8 | 451 | 420 | 9 | 9 | 8 | 539 | 550 |
| 17 | 7 | 7 | 586 | 587 | −26 | 0 | 8 | 638 | 638 | −4 | 6 | 8 | 859 | 834 | 13 | 9 | 8 | 165 | 160 |
| 19 | 7 | 7 | 816 | 799 | −24 | 0 | 8 | 668 | 642 | −2 | 6 | 8 | 1324 | 1285 | −6 | 10 | 8 | 520 | 508 |
| −20 | 8 | 7 | 341 | 342 | −22 | 0 | 8 | 1188 | 1184 | 0 | 6 | 8 | 833 | 802 | −2 | 10 | 8 | 155 | 155 |
| −18 | 8 | 7 | 436 | 435 | −20 | 0 | 8 | 582 | 578 | 2 | 6 | 8 | 1351 | 1328 | 0 | 10 | 8 | 184 | 212 |
| −16 | 8 | 7 | 616 | 619 | −18 | 0 | 8 | 788 | 809 | 4 | 6 | 8 | 229 | 199 | 2 | 10 | 8 | 899 | 904 |
| −14 | 8 | 7 | 400 | 383 | −16 | 0 | 8 | 1137 | 1175 | 6 | 6 | 8 | 772 | 753 | 4 | 10 | 8 | 807 | 795 |
| −12 | 8 | 7 | 251 | 231 | −14 | 0 | 8 | 2316 | 2373 | 8 | 6 | 8 | 1250 | 1221 | 6 | 10 | 8 | 255 | 262 |
| −10 | 8 | 7 | 584 | 548 | −12 | 0 | 8 | 2541 | 2449 | 10 | 6 | 8 | 1509 | 1503 | 10 | 10 | 8 | 662 | 664 |
| −8 | 8 | 7 | 629 | 616 | −10 | 0 | 8 | 157 | 88 | 12 | 6 | 8 | 963 | 957 | 12 | 10 | 8 | 713 | 717 |
| −6 | 8 | 7 | 345 | 319 | −8 | 0 | 8 | 522 | 502 | 16 | 6 | 8 | 652 | 651 | −13 | 11 | 8 | 581 | 554 |
| −2 | 8 | 7 | 452 | 444 | −6 | 0 | 8 | 1469 | 1416 | 18 | 6 | 8 | 865 | 867 | −11 | 11 | 8 | 553 | 557 |
| 0 | 8 | 7 | 185 | 164 | −4 | 0 | 8 | 2818 | 2791 | −19 | 7 | 8 | 188 | 207 | −9 | 11 | 8 | 568 | 566 |
| 10 | 8 | 7 | 160 | 171 | −2 | 0 | 8 | 1987 | 2059 | −15 | 7 | 8 | 476 | 473 | −7 | 11 | 8 | 248 | 256 |
| 0 | 0 | 8 | 861 | 849 | −17 | 3 | 8 | 182 | 177 | −13 | 7 | 8 | 444 | 472 | −5 | 11 | 8 | 722 | 709 |
| 2 | 0 | 8 | 663 | 691 | −15 | 3 | 8 | 182 | 160 | −11 | 7 | 8 | 550 | 554 | −3 | 11 | 8 | 698 | 677 |
| 4 | 0 | 8 | 240 | 245 | −13 | 3 | 8 | 481 | 502 | −9 | 7 | 8 | 977 | 957 | −1 | 11 | 8 | 1117 | 1123 |
| 6 | 0 | 8 | 1909 | 1960 | −11 | 3 | 8 | 237 | 243 | −7 | 7 | 8 | 174 | 177 | 1 | 11 | 8 | 673 | 678 |
| 8 | 0 | 8 | 1465 | 1506 | −9 | 3 | 8 | 904 | 925 | −5 | 7 | 8 | 676 | 658 | 5 | 11 | 8 | 261 | 255 |
| 10 | 0 | 8 | 1634 | 1603 | −3 | 3 | 8 | 322 | 327 | −3 | 7 | 8 | 687 | 680 | 7 | 11 | 8 | 753 | 758 |
| 12 | 0 | 8 | 1202 | 1199 | −1 | 3 | 8 | 578 | 590 | −1 | 7 | 8 | 1389 | 1370 | 9 | 11 | 8 | 888 | 906 |
| 14 | 0 | 8 | 311 | 301 | 1 | 3 | 8 | 301 | 295 | 1 | 7 | 8 | 707 | 711 | −8 | 12 | 8 | 202 | 201 |
| 16 | 0 | 8 | 1016 | 1041 | 3 | 3 | 8 | 717 | 760 | 3 | 7 | 8 | 507 | 512 | 0 | 12 | 8 | 461 | 474 |
| 18 | 0 | 8 | 657 | 650 | 5 | 3 | 8 | 463 | 458 | 7 | 7 | 8 | 379 | 372 | −25 | 1 | 9 | 710 | 688 |
| 20 | 0 | 8 | 776 | 771 | 7 | 3 | 8 | 811 | 830 | 9 | 7 | 8 | 532 | 549 | −23 | 1 | 9 | 841 | 844 |
| 22 | 0 | 8 | 240 | 243 | 9 | 3 | 8 | 597 | 594 | 13 | 7 | 8 | 165 | 137 | −21 | 1 | 9 | 199 | 241 |
| −21 | 1 | 8 | 242 | 219 | 11 | 3 | 8 | 840 | 845 | 15 | 7 | 8 | 346 | 348 | −19 | 1 | 9 | 710 | 713 |
| −19 | 1 | 8 | 316 | 321 | 13 | 3 | 8 | 191 | 168 | 17 | 7 | 8 | 172 | 132 | −17 | 1 | 9 | 878 | 892 |
| −17 | 1 | 8 | 252 | 257 | 15 | 3 | 8 | 1095 | 1106 | −20 | 8 | 8 | 188 | 117 | −15 | 1 | 9 | 1225 | 1219 |
| −15 | 1 | 8 | 414 | 438 | 17 | 3 | 8 | 1003 | 1004 | −16 | 8 | 8 | 203 | 229 | −13 | 1 | 9 | 1122 | 1118 |
| −13 | 1 | 8 | 297 | 297 | 19 | 3 | 8 | 682 | 667 | −10 | 8 | 8 | 527 | 496 | −11 | 1 | 9 | 235 | 232 |
| −11 | 1 | 8 | 542 | 561 | 21 | 3 | 8 | 279 | 308 | −8 | 8 | 8 | 219 | 207 | −9 | 1 | 9 | 323 | 339 |
| −9 | 1 | 8 | 591 | 583 | −24 | 4 | 8 | 219 | 215 | −6 | 8 | 8 | 474 | 467 | −7 | 1 | 9 | 242 | 219 |
| −5 | 1 | 8 | 181 | 239 | −22 | 4 | 8 | 625 | 629 | −4 | 8 | 8 | 272 | 247 | −5 | 1 | 9 | 1208 | 1231 |
| −3 | 1 | 8 | 229 | 227 | −20 | 4 | 8 | 296 | 273 | −2 | 8 | 8 | 390 | 370 | −3 | 1 | 9 | 1266 | 1278 |
| −1 | 1 | 8 | 504 | 516 | −18 | 4 | 8 | 529 | 540 | 0 | 8 | 8 | 789 | 798 | −1 | 1 | 9 | 613 | 648 |
| 3 | 1 | 8 | 307 | 310 | −16 | 4 | 8 | 352 | 379 | 2 | 8 | 8 | 195 | 201 | 1 | 1 | 9 | 933 | 954 |
| 5 | 1 | 8 | 243 | 232 | −14 | 4 | 8 | 942 | 951 | 4 | 8 | 8 | 485 | 485 | 3 | 1 | 9 | 207 | 207 |
| 7 | 1 | 8 | 586 | 579 | −12 | 4 | 8 | 1293 | 1297 | 6 | 8 | 8 | 491 | 503 | 5 | 1 | 9 | 1154 | 1178 |
| 11 | 1 | 8 | 410 | 405 | −8 | 4 | 8 | 199 | 209 | 8 | 8 | 8 | 822 | 816 | 7 | 1 | 9 | 874 | 860 |
| 13 | 1 | 8 | 158 | 161 | −6 | 4 | 8 | 307 | 314 | 10 | 8 | 8 | 573 | 571 | 9 | 1 | 9 | 669 | 668 |
| 15 | 1 | 8 | 823 | 836 | −4 | 4 | 8 | 1113 | 1130 | 12 | 8 | 8 | 324 | 319 | 11 | 1 | 9 | 725 | 740 |
| 17 | 1 | 8 | 506 | 526 | −2 | 4 | 8 | 810 | 818 | 14 | 8 | 8 | 355 | 353 | 13 | 1 | 9 | 290 | 312 |
| 19 | 1 | 8 | 508 | 503 | 0 | 4 | 8 | 232 | 256 | 16 | 8 | 8 | 576 | 583 | 15 | 1 | 9 | 483 | 498 |
| 21 | 1 | 8 | 202 | 181 | 2 | 4 | 8 | 842 | 872 | −17 | 9 | 8 | 313 | 304 | 19 | 1 | 9 | 288 | 327 |
| −26 | 2 | 8 | 223 | 203 | 4 | 4 | 8 | 377 | 398 | −15 | 9 | 8 | 480 | 477 | 21 | 1 | 9 | 177 | 148 |
| −24 | 2 | 8 | 371 | 349 | 6 | 4 | 8 | 676 | 659 | −13 | 9 | 8 | 479 | 479 | −24 | 2 | 9 | 170 | 118 |
| −22 | 2 | 8 | 354 | 359 | 8 | 4 | 8 | 367 | 335 | −20 | 2 | 9 | 775 | 767 | −17 | 5 | 9 | 691 | 702 |
| −18 | 2 | 8 | 238 | 248 | 10 | 4 | 8 | 513 | 507 | −18 | 2 | 9 | 705 | 701 | −15 | 5 | 9 | 678 | 699 |
| −16 | 2 | 8 | 412 | 421 | 12 | 4 | 8 | 993 | 1002 | −12 | 2 | 9 | 978 | 978 | −13 | 5 | 9 | 801 | 828 |
| −14 | 2 | 8 | 529 | 544 | 16 | 4 | 8 | 179 | 179 | −10 | 2 | 9 | 1311 | 1299 | −11 | 5 | 9 | 223 | 176 |
| −12 | 2 | 8 | 509 | 491 | 20 | 4 | 8 | 361 | 355 | −8 | 2 | 9 | 226 | 185 | −7 | 5 | 9 | 467 | 467 |
| −10 | 2 | 8 | 442 | 437 | −23 | 5 | 8 | 570 | 559 | −6 | 2 | 9 | 284 | 305 | −5 | 5 | 9 | 454 | 447 |
| −8 | 2 | 8 | 159 | 133 | −21 | 5 | 8 | 301 | 331 | −4 | 2 | 9 | 166 | 133 | −3 | 5 | 9 | 853 | 826 |
| −6 | 2 | 8 | 263 | 224 | −17 | 5 | 8 | 393 | 407 | −2 | 2 | 9 | 213 | 223 | −1 | 5 | 9 | 551 | 537 |
| −4 | 2 | 8 | 344 | 352 | −15 | 5 | 8 | 1073 | 1085 | 0 | 2 | 9 | 349 | 321 | 1 | 5 | 9 | 1425 | 1391 |
| −2 | 2 | 8 | 1015 | 1010 | −13 | 5 | 8 | 794 | 792 | 2 | 2 | 9 | 442 | 441 | 3 | 5 | 9 | 456 | 441 |
| 0 | 2 | 8 | 476 | 509 | −11 | 5 | 8 | 1018 | 1021 | 4 | 2 | 9 | 1032 | 1056 | 5 | 5 | 9 | 564 | 555 |
| 2 | 2 | 8 | 893 | 909 | −9 | 5 | 8 | 432 | 423 | 6 | 2 | 9 | 1509 | 1472 | 7 | 5 | 9 | 575 | 579 |
| 4 | 2 | 8 | 209 | 213 | −7 | 5 | 8 | 921 | 953 | 8 | 2 | 9 | 434 | 434 | 9 | 5 | 9 | 667 | 670 |
| 6 | 2 | 8 | 601 | 625 | −5 | 5 | 8 | 1199 | 1224 | 10 | 2 | 9 | 532 | 538 | 11 | 5 | 9 | 792 | 778 |
| 8 | 2 | 8 | 762 | 774 | −3 | 5 | 8 | 1343 | 1359 | 12 | 2 | 9 | 316 | 302 | 15 | 5 | 9 | 227 | 259 |
| 10 | 2 | 8 | 801 | 798 | −1 | 5 | 8 | 1167 | 1207 | 14 | 2 | 9 | 1475 | 1495 | −22 | 6 | 9 | 184 | 198 |
| 12 | 2 | 8 | 539 | 558 | 1 | 5 | 8 | 295 | 316 | 16 | 2 | 9 | 830 | 832 | −20 | 6 | 9 | 354 | 350 |

TABLE 1-continued

MO2CO2S4(CO)2(NCCH3)2[S2CH(C2H5)2]2

| H | K | L | FOBS | FCAL | H | K | L | FOBS | FCAL | H | K | L | FOBS | FCAL | H | K | L | FOBS | FCAL |
|---|---|---|------|------|---|---|---|------|------|---|---|---|------|------|---|---|---|------|------|
| 18 | 2 | 9 | 567 | 588 | −16 | 6 | 9 | 746 | 764 | −4 | 0 | 10 | 1070 | 1101 | 15 | 3 | 10 | 641 | 662 |
| 20 | 2 | 9 | 298 | 281 | −14 | 6 | 9 | 751 | 772 | −2 | 0 | 10 | 221 | 234 | 17 | 3 | 10 | 232 | 238 |
| −19 | 3 | 9 | 180 | 167 | −12 | 6 | 9 | 698 | 705 | 0 | 0 | 10 | 389 | 383 | −22 | 4 | 10 | 187 | 178 |
| −17 | 3 | 9 | 204 | 207 | −10 | 6 | 9 | 607 | 588 | 2 | 0 | 10 | 475 | 483 | −20 | 4 | 10 | 223 | 218 |
| −9 | 3 | 9 | 221 | 174 | −8 | 6 | 9 | 524 | 504 | 4 | 0 | 10 | 1544 | 1490 | −18 | 4 | 10 | 201 | 186 |
| −7 | 3 | 9 | 251 | 240 | −6 | 6 | 9 | 835 | 798 | 6 | 0 | 10 | 520 | 529 | −16 | 4 | 10 | 236 | 225 |
| −5 | 3 | 9 | 155 | 158 | −4 | 6 | 9 | 631 | 604 | 8 | 0 | 10 | 678 | 686 | −14 | 4 | 10 | 448 | 467 |
| −1 | 3 | 9 | 185 | 185 | −2 | 6 | 9 | 934 | 912 | 10 | 0 | 10 | 225 | 214 | −8 | 4 | 10 | 454 | 466 |
| 1 | 3 | 9 | 208 | 204 | 0 | 6 | 9 | 355 | 359 | 12 | 0 | 10 | 551 | 560 | −4 | 4 | 10 | 454 | 459 |
| 3 | 3 | 9 | 898 | 930 | 2 | 6 | 9 | 710 | 684 | 16 | 0 | 10 | 509 | 500 | −2 | 4 | 10 | 348 | 328 |
| 7 | 3 | 9 | 556 | 538 | 8 | 6 | 9 | 436 | 432 | 18 | 0 | 10 | 199 | 217 | 0 | 4 | 10 | 394 | 387 |
| 9 | 3 | 9 | 312 | 316 | 10 | 6 | 9 | 220 | 229 | −21 | 1 | 10 | 464 | 458 | 2 | 4 | 10 | 428 | 422 |
| 11 | 3 | 9 | 541 | 534 | 14 | 6 | 9 | 334 | 338 | −19 | 1 | 10 | 557 | 554 | 4 | 4 | 10 | 229 | 232 |
| 15 | 3 | 9 | 378 | 384 | −19 | 7 | 9 | 297 | 285 | −17 | 1 | 10 | 199 | 226 | 6 | 4 | 10 | 677 | 659 |
| 17 | 3 | 9 | 465 | 485 | −17 | 7 | 9 | 492 | 507 | −13 | 1 | 10 | 339 | 341 | 8 | 4 | 10 | 479 | 488 |
| −24 | 4 | 9 | 452 | 444 | −15 | 7 | 9 | 273 | 292 | −11 | 1 | 10 | 713 | 705 | 14 | 4 | 10 | 401 | 401 |
| −22 | 4 | 9 | 199 | 183 | −13 | 7 | 9 | 184 | 189 | 16 | 4 | 10 | 720 | 722 | 0 | 8 | 10 | 797 | 792 |
| −20 | 4 | 9 | 441 | 436 | −11 | 7 | 9 | 193 | 182 | 18 | 4 | 10 | 242 | 241 | 2 | 8 | 10 | 926 | 937 |
| −18 | 4 | 9 | 883 | 889 | −7 | 7 | 9 | 271 | 286 | −19 | 5 | 10 | 521 | 538 | 4 | 8 | 10 | 813 | 820 |
| −16 | 4 | 9 | 822 | 843 | −5 | 7 | 9 | 523 | 513 | −17 | 5 | 10 | 859 | 877 | 6 | 8 | 10 | 720 | 729 |
| −14 | 4 | 9 | 458 | 460 | −3 | 7 | 9 | 367 | 364 | −15 | 5 | 10 | 830 | 840 | 8 | 8 | 10 | 330 | 346 |
| −12 | 4 | 9 | 228 | 200 | −1 | 7 | 9 | 629 | 608 | −13 | 5 | 10 | 301 | 338 | 10 | 8 | 10 | 428 | 432 |
| −10 | 4 | 9 | 921 | 913 | 1 | 7 | 9 | 222 | 226 | −11 | 5 | 10 | 392 | 357 | 12 | 8 | 10 | 583 | 576 |
| −8 | 4 | 9 | 938 | 928 | 3 | 7 | 9 | 259 | 276 | −9 | 5 | 10 | 786 | 784 | −15 | 9 | 10 | 437 | 458 |
| −6 | 4 | 9 | 1003 | 1037 | 5 | 7 | 9 | 429 | 451 | −7 | 5 | 10 | 1346 | 1299 | −11 | 9 | 10 | 398 | 401 |
| −4 | 4 | 9 | 1124 | 1155 | 7 | 7 | 9 | 904 | 906 | −5 | 5 | 10 | 661 | 632 | −9 | 9 | 10 | 824 | 801 |
| −2 | 4 | 9 | 238 | 258 | 9 | 7 | 9 | 801 | 798 | −3 | 5 | 10 | 329 | 291 | −7 | 9 | 10 | 879 | 848 |
| 0 | 4 | 9 | 150 | 140 | 13 | 7 | 9 | 255 | 210 | −1 | 5 | 10 | 315 | 295 | −5 | 9 | 10 | 554 | 528 |
| 2 | 4 | 9 | 828 | 830 | 15 | 7 | 9 | 617 | 620 | 1 | 5 | 10 | 1219 | 1181 | −1 | 9 | 10 | 492 | 487 |
| 4 | 4 | 9 | 1261 | 1246 | −18 | 8 | 9 | 488 | 500 | 3 | 5 | 10 | 586 | 555 | 1 | 9 | 10 | 753 | 749 |
| 6 | 4 | 9 | 993 | 979 | −12 | 8 | 9 | 436 | 423 | 5 | 5 | 10 | 386 | 395 | 3 | 9 | 10 | 674 | 681 |
| 8 | 4 | 9 | 625 | 618 | −10 | 8 | 9 | 918 | 899 | 7 | 5 | 10 | 243 | 230 | 5 | 9 | 10 | 357 | 360 |
| 12 | 4 | 9 | 595 | 601 | −8 | 8 | 9 | 370 | 363 | 9 | 5 | 10 | 496 | 484 | 9 | 9 | 10 | 333 | 346 |
| 14 | 4 | 9 | 821 | 825 | −2 | 8 | 9 | 503 | 487 | 11 | 5 | 10 | 402 | 391 | 11 | 9 | 10 | 371 | 349 |
| 16 | 4 | 9 | 790 | 802 | 0 | 8 | 9 | 243 | 235 | 13 | 5 | 10 | 221 | 237 | −10 | 10 | 10 | 425 | 391 |
| 18 | 4 | 9 | 331 | 318 | 2 | 8 | 9 | 271 | 276 | 15 | 5 | 10 | 238 | 216 | −8 | 10 | 10 | 799 | 770 |
| −23 | 5 | 9 | 598 | 597 | 4 | 8 | 9 | 471 | 482 | −20 | 6 | 10 | 406 | 442 | −6 | 10 | 10 | 373 | 356 |
| −21 | 5 | 9 | 188 | 178 | 6 | 8 | 9 | 293 | 285 | −18 | 6 | 10 | 426 | 465 | −2 | 10 | 10 | 232 | 232 |
| −19 | 5 | 9 | 530 | 563 | 10 | 8 | 9 | 154 | 127 | −16 | 6 | 10 | 372 | 355 | 0 | 10 | 10 | 516 | 523 |
| 12 | 8 | 9 | 293 | 280 | −9 | 1 | 10 | 634 | 622 | −14 | 6 | 10 | 539 | 561 | 2 | 10 | 10 | 544 | 567 |
| 14 | 8 | 9 | 439 | 433 | −7 | 1 | 10 | 342 | 347 | −8 | 6 | 10 | 277 | 233 | 4 | 10 | 10 | 253 | 266 |
| −17 | 9 | 9 | 311 | 292 | −5 | 1 | 10 | 931 | 937 | −6 | 6 | 10 | 796 | 763 | 6 | 10 | 10 | 261 | 224 |
| −15 | 9 | 9 | 426 | 432 | −1 | 1 | 10 | 609 | 632 | −4 | 6 | 10 | 572 | 546 | 8 | 10 | 10 | 170 | 58 |
| −9 | 9 | 9 | 497 | 490 | 1 | 1 | 10 | 282 | 292 | −2 | 6 | 10 | 327 | 345 | −7 | 11 | 10 | 418 | 381 |
| −7 | 9 | 9 | 1112 | 1083 | 3 | 1 | 10 | 1326 | 1360 | 2 | 6 | 10 | 519 | 509 | −5 | 11 | 10 | 351 | 338 |
| −5 | 9 | 9 | 498 | 491 | 5 | 1 | 10 | 1158 | 1159 | 4 | 6 | 10 | 565 | 578 | −3 | 11 | 10 | 483 | 481 |
| −3 | 9 | 9 | 273 | 276 | 11 | 1 | 10 | 551 | 567 | 6 | 6 | 10 | 494 | 524 | −1 | 11 | 10 | 273 | 238 |
| 1 | 9 | 9 | 1143 | 1136 | 13 | 1 | 10 | 983 | 1004 | 12 | 6 | 10 | 331 | 324 | 1 | 11 | 10 | 161 | 164 |
| 3 | 9 | 9 | 1128 | 1142 | 15 | 1 | 10 | 356 | 356 | 14 | 6 | 10 | 336 | 365 | 3 | 11 | 10 | 210 | 128 |
| 5 | 9 | 9 | 578 | 571 | 17 | 1 | 10 | 242 | 263 | 19 | 7 | 10 | 405 | 391 | −23 | 1 | 11 | 257 | 269 |
| 7 | 9 | 9 | 427 | 414 | −20 | 2 | 10 | 228 | 254 | 17 | 7 | 10 | 170 | 126 | −21 | 1 | 11 | 216 | 223 |
| 9 | 9 | 9 | 223 | 215 | −18 | 2 | 10 | 386 | 381 | 15 | 7 | 10 | 191 | 211 | −19 | 1 | 11 | 394 | 382 |
| 11 | 9 | 9 | 701 | 698 | −16 | 2 | 10 | 385 | 369 | 13 | 7 | 10 | 407 | 408 | −17 | 1 | 11 | 569 | 570 |
| 13 | 9 | 9 | 582 | 594 | −14 | 2 | 10 | 485 | 445 | 11 | 7 | 10 | 855 | 860 | −15 | 1 | 11 | 827 | 813 |
| −14 | 10 | 9 | 598 | 599 | −8 | 2 | 10 | 297 | 259 | −5 | 7 | 10 | 293 | 277 | −13 | 1 | 11 | 339 | 328 |
| −12 | 10 | 9 | 395 | 369 | −6 | 2 | 10 | 574 | 588 | −3 | 7 | 10 | 352 | 345 | −11 | 1 | 11 | 535 | 521 |
| −10 | 10 | 9 | 169 | 168 | −4 | 2 | 10 | 370 | 403 | −1 | 7 | 10 | 519 | 499 | −9 | 1 | 11 | 722 | 696 |
| −8 | 10 | 9 | 648 | 631 | −2 | 2 | 10 | 249 | 235 | 1 | 7 | 10 | 425 | 422 | −7 | 1 | 11 | 1110 | 1121 |
| −6 | 10 | 9 | 918 | 884 | 2 | 2 | 10 | 418 | 415 | 3 | 7 | 10 | 694 | 679 | −5 | 1 | 11 | 832 | 834 |
| −4 | 10 | 9 | 559 | 558 | 4 | 2 | 10 | 381 | 359 | 5 | 7 | 10 | 452 | 452 | −3 | 1 | 11 | 697 | 693 |
| −2 | 10 | 9 | 658 | 665 | 6 | 2 | 10 | 586 | 585 | 7 | 7 | 10 | 301 | 287 | −1 | 1 | 11 | 1031 | 981 |
| 2 | 10 | 9 | 455 | 470 | 12 | 2 | 10 | 284 | 314 | 9 | 7 | 10 | 290 | 249 | 1 | 1 | 11 | 1063 | 1029 |
| 4 | 10 | 9 | 414 | 402 | 14 | 2 | 10 | 336 | 350 | 11 | 7 | 10 | 257 | 249 | 3 | 1 | 11 | 924 | 921 |
| 6 | 10 | 9 | 504 | 504 | −21 | 3 | 10 | 780 | 777 | 13 | 7 | 10 | 423 | 418 | 5 | 1 | 11 | 538 | 521 |
| 8 | 10 | 9 | 513 | 516 | −19 | 3 | 10 | 1052 | 1040 | 18 | 8 | 10 | 502 | 497 | 7 | 1 | 11 | 938 | 940 |
| −7 | 11 | 9 | 265 | 274 | −17 | 3 | 10 | 488 | 499 | 16 | 8 | 10 | 542 | 560 | 9 | 1 | 11 | 660 | 678 |
| −5 | 11 | 9 | 263 | 286 | −15 | 3 | 10 | 308 | 328 | 14 | 8 | 10 | 179 | 144 | 11 | 1 | 11 | 553 | 565 |
| −1 | 11 | 9 | 374 | 367 | −11 | 3 | 10 | 1063 | 1103 | 10 | 8 | 10 | 542 | 529 | 15 | 1 | 11 | 328 | 343 |
| 1 | 11 | 9 | 403 | 402 | −9 | 3 | 10 | 966 | 956 | −8 | 8 | 10 | 1016 | 985 | 17 | 1 | 11 | 287 | 302 |
| 3 | 11 | 9 | 383 | 368 | −7 | 3 | 10 | 1271 | 1274 | −6 | 8 | 10 | 766 | 748 | −22 | 2 | 11 | 281 | 267 |
| −24 | 0 | 10 | 689 | 670 | −5 | 3 | 10 | 1447 | 1378 | −4 | 8 | 10 | 474 | 453 | −20 | 2 | 11 | 606 | 590 |
| −20 | 0 | 10 | 771 | 779 | −3 | 3 | 10 | 212 | 242 | −2 | 8 | 10 | 256 | 249 | −18 | 2 | 11 | 419 | 401 |
| −18 | 0 | 10 | 870 | 848 | −1 | 3 | 10 | 652 | 683 | −16 | 2 | 11 | 649 | 636 | −5 | 5 | 11 | 555 | 514 |
| −16 | 0 | 10 | 831 | 818 | 1 | 3 | 10 | 1254 | 1224 | −14 | 2 | 11 | 688 | 686 | −3 | 5 | 11 | 550 | 529 |
| −14 | 0 | 10 | 909 | 900 | 3 | 3 | 10 | 2069 | 2038 | −12 | 2 | 11 | 406 | 387 | −1 | 5 | 11 | 626 | 614 |
| −12 | 0 | 10 | 202 | 212 | 5 | 3 | 10 | 1702 | 1689 | −10 | 2 | 11 | 1037 | 1023 | 1 | 5 | 11 | 438 | 420 |
| −10 | 0 | 10 | 599 | 575 | 9 | 3 | 10 | 185 | 222 | −8 | 2 | 11 | 1539 | 1534 | 3 | 5 | 11 | 436 | 426 |
| −8 | 0 | 10 | 416 | 419 | 11 | 3 | 10 | 799 | 809 | −6 | 2 | 11 | 2132 | 2120 | 5 | 5 | 11 | 443 | 443 |
| −6 | 0 | 10 | 1285 | 1259 | 13 | 3 | 10 | 1207 | 1219 | −4 | 2 | 11 | 805 | 777 | 7 | 5 | 11 | 889 | 897 |

TABLE 1-continued

MO2CO2S4(CO)2(NCCH3)2[S2CH(C2H5)2]2

| H | K | L | FOBS | FCAL | H | K | L | FOBS | FCAL | H | K | L | FOBS | FCAL | H | K | L | FOBS | FCAL |
|---|---|---|------|------|---|---|---|------|------|---|---|---|------|------|---|---|---|------|------|
| −2 | 2 | 11 | 837 | 776 | 9 | 5 | 11 | 309 | 338 | 11 | 1 | 12 | 689 | 674 | 8 | 4 | 12 | 225 | 234 |
| 0 | 2 | 11 | 1058 | 1011 | 11 | 5 | 11 | 301 | 303 | −9 | 1 | 12 | 875 | 874 | 14 | 4 | 12 | 425 | 419 |
| 2 | 2 | 11 | 2332 | 2302 | 15 | 5 | 11 | 500 | 506 | −7 | 1 | 12 | 1142 | 1148 | −19 | 5 | 12 | 500 | 485 |
| 4 | 2 | 11 | 1530 | 1514 | −18 | 6 | 11 | 302 | 290 | −5 | 1 | 12 | 424 | 386 | −17 | 5 | 12 | 378 | 358 |
| 6 | 2 | 11 | 336 | 337 | −16 | 6 | 11 | 179 | 166 | −3 | 1 | 12 | 323 | 311 | −13 | 5 | 12 | 327 | 347 |
| 10 | 2 | 11 | 662 | 664 | −10 | 6 | 11 | 191 | 197 | −1 | 1 | 12 | 634 | 610 | −11 | 5 | 12 | 748 | 730 |
| 12 | 2 | 11 | 1014 | 1036 | −6 | 6 | 11 | 479 | 477 | 1 | 1 | 12 | 1012 | 1009 | −9 | 5 | 12 | 788 | 786 |
| 14 | 2 | 11 | 663 | 681 | −4 | 6 | 11 | 277 | 261 | 3 | 1 | 12 | 678 | 655 | −7 | 5 | 12 | 308 | 292 |
| 16 | 2 | 11 | 263 | 293 | 2 | 6 | 11 | 359 | 359 | 5 | 1 | 12 | 402 | 382 | −5 | 5 | 12 | 260 | 223 |
| 18 | 2 | 11 | 229 | 247 | 4 | 6 | 11 | 463 | 464 | 7 | 1 | 12 | 179 | 128 | −3 | 5 | 12 | 705 | 690 |
| −23 | 3 | 11 | 187 | 198 | 8 | 6 | 11 | 230 | 203 | 11 | 1 | 12 | 564 | 571 | −1 | 5 | 12 | 813 | 805 |
| −17 | 3 | 11 | 214 | 186 | 10 | 6 | 11 | 183 | 159 | 13 | 1 | 12 | 456 | 483 | 1 | 5 | 12 | 636 | 646 |
| −13 | 3 | 11 | 231 | 221 | 12 | 6 | 11 | 167 | 146 | 15 | 1 | 12 | 205 | 136 | 3 | 5 | 12 | 183 | 171 |
| −9 | 3 | 11 | 673 | 672 | −19 | 7 | 11 | 303 | 338 | −20 | 2 | 12 | 199 | 172 | 5 | 5 | 12 | 267 | 292 |
| −7 | 3 | 11 | 233 | 215 | −17 | 7 | 11 | 490 | 488 | −18 | 2 | 12 | 211 | 208 | 7 | 5 | 12 | 475 | 472 |
| −3 | 3 | 11 | 363 | 367 | −15 | 7 | 11 | 363 | 347 | −16 | 2 | 12 | 329 | 297 | 9 | 5 | 12 | 614 | 612 |
| −1 | 3 | 11 | 333 | 291 | −11 | 7 | 11 | 259 | 304 | −12 | 2 | 12 | 289 | 289 | 11 | 5 | 12 | 324 | 352 |
| 1 | 3 | 11 | 288 | 287 | −9 | 7 | 11 | 684 | 681 | −10 | 2 | 12 | 587 | 582 | −18 | 6 | 12 | 281 | 302 |
| 3 | 3 | 11 | 405 | 403 | −7 | 7 | 11 | 817 | 799 | −8 | 2 | 12 | 511 | 524 | −16 | 6 | 12 | 400 | 434 |
| 5 | 3 | 11 | 803 | 811 | −5 | 7 | 11 | 642 | 625 | −6 | 2 | 12 | 429 | 421 | −12 | 6 | 12 | 454 | 446 |
| 7 | 3 | 11 | 359 | 386 | −3 | 7 | 11 | 310 | 236 | −4 | 2 | 12 | 360 | 330 | −10 | 6 | 12 | 631 | 634 |
| 11 | 3 | 11 | 310 | 342 | −1 | 7 | 11 | 625 | 629 | −2 | 2 | 12 | 515 | 501 | −8 | 6 | 12 | 630 | 644 |
| 13 | 3 | 11 | 519 | 539 | 1 | 7 | 11 | 881 | 876 | 0 | 2 | 12 | 667 | 653 | −6 | 6 | 12 | 479 | 467 |
| 15 | 3 | 11 | 442 | 445 | 3 | 7 | 11 | 922 | 921 | 2 | 2 | 12 | 588 | 571 | −4 | 6 | 12 | 522 | 510 |
| 17 | 3 | 11 | 270 | 239 | 5 | 7 | 11 | 568 | 549 | 6 | 2 | 12 | 261 | 255 | −2 | 6 | 12 | 867 | 857 |
| −22 | 4 | 11 | 326 | 321 | 9 | 7 | 11 | 434 | 444 | 8 | 2 | 12 | 314 | 326 | 0 | 6 | 12 | 786 | 787 |
| −20 | 4 | 11 | 681 | 672 | 11 | 7 | 11 | 587 | 604 | 2 | 6 | 12 | 735 | 738 | −8 | 2 | 13 | 1042 | 1036 |
| −18 | 4 | 11 | 813 | 807 | 13 | 7 | 11 | 532 | 549 | 6 | 6 | 12 | 540 | 533 | −6 | 2 | 13 | 858 | 834 |
| −16 | 4 | 11 | 878 | 873 | −16 | 8 | 11 | 489 | 506 | 8 | 6 | 12 | 504 | 517 | −2 | 2 | 13 | 207 | 210 |
| −14 | 4 | 11 | 279 | 261 | −14 | 8 | 11 | 312 | 304 | 10 | 6 | 12 | 775 | 786 | 0 | 2 | 13 | 646 | 629 |
| −12 | 4 | 11 | 542 | 560 | −12 | 8 | 11 | 308 | 286 | 12 | 6 | 12 | 519 | 541 | 2 | 2 | 13 | 1190 | 1188 |
| −10 | 4 | 11 | 1253 | 1255 | −10 | 8 | 11 | 776 | 725 | −17 | 7 | 12 | 354 | 341 | 4 | 2 | 13 | 769 | 771 |
| −8 | 4 | 11 | 1611 | 1584 | −8 | 8 | 11 | 1026 | 1003 | −15 | 7 | 12 | 481 | 486 | 6 | 2 | 13 | 177 | 155 |
| −6 | 4 | 11 | 1377 | 1352 | −6 | 8 | 11 | 930 | 915 | −11 | 7 | 12 | 417 | 391 | 10 | 2 | 13 | 896 | 892 |
| −4 | 4 | 11 | 478 | 453 | −4 | 8 | 11 | 186 | 134 | −9 | 7 | 12 | 504 | 489 | 12 | 2 | 13 | 706 | 729 |
| −2 | 4 | 11 | 943 | 934 | −2 | 8 | 11 | 639 | 638 | −7 | 7 | 12 | 723 | 721 | −19 | 3 | 13 | 179 | 158 |
| 0 | 4 | 11 | 1665 | 1638 | 0 | 8 | 11 | 851 | 826 | −5 | 7 | 12 | 354 | 356 | −11 | 3 | 13 | 206 | 168 |
| 2 | 4 | 11 | 1490 | 1469 | 2 | 8 | 11 | 791 | 785 | −3 | 7 | 12 | 257 | 247 | −9 | 3 | 13 | 368 | 364 |
| 4 | 4 | 11 | 1172 | 1148 | 4 | 8 | 11 | 531 | 544 | 1 | 7 | 12 | 248 | 276 | −7 | 3 | 13 | 290 | 315 |
| 6 | 4 | 11 | 250 | 232 | 6 | 8 | 11 | 189 | 184 | 3 | 7 | 12 | 541 | 526 | −5 | 3 | 13 | 371 | 339 |
| 8 | 4 | 11 | 548 | 560 | 8 | 8 | 11 | 305 | 302 | 7 | 7 | 12 | 272 | 284 | −1 | 3 | 13 | 435 | 424 |
| 10 | 4 | 11 | 711 | 721 | 10 | 8 | 11 | 172 | 152 | 9 | 7 | 12 | 247 | 234 | 1 | 3 | 13 | 464 | 462 |
| 12 | 4 | 11 | 750 | 756 | −13 | 9 | 11 | 320 | 294 | −12 | 8 | 12 | 367 | 356 | 3 | 3 | 13 | 220 | 190 |
| 14 | 4 | 11 | 357 | 321 | −11 | 9 | 11 | 610 | 599 | −10 | 8 | 12 | 779 | 757 | 5 | 3 | 13 | 259 | 265 |
| −17 | 5 | 11 | 176 | 154 | −9 | 9 | 11 | 926 | 923 | −8 | 8 | 12 | 839 | 850 | 7 | 3 | 13 | 208 | 208 |
| −15 | 5 | 11 | 695 | 718 | −7 | 9 | 11 | 550 | 556 | −6 | 8 | 12 | 406 | 404 | 9 | 3 | 13 | 229 | 250 |
| −13 | 5 | 11 | 378 | 350 | −1 | 9 | 11 | 429 | 435 | −4 | 8 | 12 | 202 | 212 | −20 | 4 | 13 | 457 | 456 |
| −9 | 5 | 11 | 355 | 359 | 1 | 9 | 11 | 759 | 774 | −2 | 8 | 12 | 333 | 354 | −18 | 4 | 13 | 441 | 410 |
| −7 | 5 | 11 | 671 | 658 | 3 | 9 | 11 | 498 | 515 | 0 | 8 | 12 | 932 | 935 | −14 | 4 | 13 | 459 | 452 |
| 5 | 9 | 11 | 545 | 547 | 10 | 2 | 12 | 500 | 507 | 2 | 8 | 12 | 808 | 823 | −12 | 4 | 13 | 773 | 789 |
| 7 | 9 | 11 | 398 | 383 | 12 | 2 | 12 | 422 | 426 | 4 | 8 | 12 | 700 | 692 | −10 | 4 | 13 | 715 | 711 |
| 9 | 9 | 11 | 346 | 363 | −21 | 3 | 12 | 534 | 509 | 6 | 8 | 12 | 281 | 274 | −8 | 4 | 13 | 635 | 606 |
| 10 | 10 | 11 | 579 | 559 | −19 | 3 | 12 | 721 | 700 | 8 | 8 | 12 | 453 | 489 | −4 | 4 | 13 | 431 | 419 |
| −8 | 10 | 11 | 680 | 666 | −17 | 3 | 12 | 907 | 886 | −11 | 9 | 12 | 566 | 566 | −2 | 4 | 13 | 615 | 591 |
| −6 | 10 | 11 | 374 | 392 | −15 | 3 | 12 | 776 | 765 | −9 | 9 | 12 | 795 | 762 | 0 | 4 | 13 | 623 | 613 |
| −2 | 10 | 11 | 341 | 344 | −13 | 3 | 12 | 459 | 400 | −7 | 9 | 12 | 596 | 570 | 2 | 4 | 13 | 631 | 642 |
| 0 | 10 | 11 | 629 | 645 | −11 | 3 | 12 | 1201 | 1226 | −3 | 9 | 12 | 447 | 467 | 8 | 4 | 13 | 514 | 527 |
| 2 | 10 | 11 | 556 | 561 | −9 | 3 | 12 | 1412 | 1406 | −1 | 9 | 12 | 631 | 646 | 10 | 4 | 13 | 608 | 633 |
| 20 | 0 | 12 | 383 | 388 | −7 | 3 | 12 | 1818 | 1771 | 1 | 9 | 12 | 611 | 604 | 12 | 4 | 13 | 421 | 418 |
| 18 | 0 | 12 | 443 | 397 | −5 | 3 | 12 | 614 | 589 | 3 | 9 | 12 | 248 | 245 | −15 | 5 | 13 | 240 | 261 |
| 16 | 0 | 12 | 603 | 557 | −3 | 3 | 12 | 702 | 690 | 0 | 10 | 12 | 274 | 227 | −13 | 5 | 13 | 662 | 664 |
| 12 | 0 | 12 | 1219 | 1196 | −1 | 3 | 12 | 1095 | 1062 | −21 | 1 | 13 | 407 | 391 | −11 | 5 | 13 | 278 | 268 |
| 10 | 0 | 12 | 826 | 814 | 1 | 3 | 12 | 1483 | 1464 | −15 | 1 | 13 | 356 | 358 | −5 | 5 | 13 | 702 | 711 |
| −8 | 0 | 12 | 841 | 846 | 3 | 3 | 12 | 1258 | 1267 | −13 | 1 | 13 | 1050 | 1026 | −3 | 5 | 13 | 747 | 732 |
| −4 | 0 | 12 | 1490 | 1496 | 5 | 3 | 12 | 313 | 298 | −11 | 1 | 13 | 603 | 601 | −1 | 5 | 13 | 355 | 356 |
| −2 | 0 | 12 | 1574 | 1561 | 9 | 3 | 12 | 448 | 462 | −9 | 1 | 13 | 281 | 281 | 1 | 5 | 13 | 432 | 431 |
| 0 | 0 | 12 | 1136 | 1090 | 11 | 3 | 12 | 859 | 871 | −7 | 1 | 13 | 273 | 207 | 5 | 5 | 13 | 434 | 446 |
| 2 | 0 | 12 | 405 | 405 | 13 | 3 | 12 | 611 | 634 | −5 | 1 | 13 | 944 | 928 | 7 | 5 | 13 | 479 | 466 |
| 4 | 0 | 12 | 717 | 700 | 15 | 3 | 12 | 192 | 202 | −3 | 1 | 13 | 1088 | 1066 | 9 | 5 | 13 | 631 | 645 |
| 6 | 0 | 12 | 1228 | 1243 | −18 | 4 | 12 | 199 | 120 | −1 | 1 | 13 | 668 | 638 | 11 | 5 | 13 | 678 | 674 |
| 8 | 0 | 12 | 1042 | 1060 | −16 | 4 | 12 | 312 | 298 | 1 | 1 | 13 | 397 | 423 | −16 | 6 | 13 | 473 | 483 |
| 10 | 0 | 12 | 597 | 623 | −14 | 4 | 12 | 218 | 153 | 5 | 1 | 13 | 692 | 678 | −14 | 6 | 13 | 223 | 241 |
| 12 | 0 | 12 | 445 | 443 | −12 | 4 | 12 | 343 | 358 | 7 | 1 | 13 | 604 | 617 | −8 | 6 | 13 | 313 | 316 |
| 14 | 0 | 12 | 321 | 320 | −6 | 4 | 12 | 190 | 197 | 9 | 1 | 13 | 791 | 809 | −6 | 6 | 13 | 440 | 442 |
| 16 | 0 | 12 | 434 | 471 | −4 | 4 | 12 | 955 | 936 | 11 | 1 | 13 | 799 | 831 | −4 | 6 | 13 | 346 | 345 |
| 21 | 1 | 12 | 354 | 312 | −2 | 4 | 12 | 671 | 644 | 15 | 1 | 13 | 207 | 224 | −2 | 6 | 13 | 567 | 574 |
| 19 | 1 | 12 | 259 | 242 | 2 | 4 | 12 | 268 | 258 | −20 | 2 | 13 | 464 | 451 | 0 | 6 | 13 | 320 | 305 |
| 17 | 1 | 12 | 438 | 432 | 4 | 4 | 12 | 773 | 794 | −18 | 2 | 13 | 556 | 518 | 2 | 6 | 13 | 311 | 327 |
| 15 | 1 | 12 | 593 | 571 | 6 | 4 | 12 | 845 | 871 | −16 | 2 | 13 | 727 | 699 | 4 | 6 | 13 | 364 | 369 |

TABLE 1-continued

MO2CO2S4(CO)2(NCCH3)2[S2CH(C2H5)2]2

| H | K | L | FOBS | FCAL | H | K | L | FOBS | FCAL | H | K | L | FOBS | FCAL | H | K | L | FOBS | FCAL |
|---|---|---|------|------|---|---|---|------|------|---|---|---|------|------|---|---|---|------|------|
| −14 | 2 | 13 | 213 | 211 | 6 | 6 | 13 | 520 | 547 | 1 | 3 | 15 | 251 | 219 | −5 | 3 | 16 | 438 | 457 |
| −12 | 2 | 13 | 597 | 581 | 8 | 6 | 13 | 435 | 459 | 5 | 3 | 15 | 186 | 179 | −1 | 3 | 16 | 181 | 182 |
| −10 | 2 | 13 | 624 | 627 | −13 | 7 | 13 | 258 | 266 | 7 | 3 | 15 | 171 | 149 | 1 | 3 | 16 | 696 | 702 |
| −11 | 7 | 13 | 520 | 514 | 8 | 7 | 13 | 521 | 531 | −16 | 4 | 15 | 334 | 347 | 3 | 3 | 16 | 849 | 874 |
| −9 | 7 | 13 | 652 | 637 | 10 | 2 | 14 | 486 | 475 | −14 | 4 | 15 | 307 | 320 | 5 | 3 | 16 | 274 | 251 |
| −7 | 7 | 13 | 255 | 281 | 12 | 2 | 14 | 177 | 134 | −10 | 4 | 15 | 176 | 106 | −10 | 4 | 16 | 213 | 158 |
| −3 | 7 | 13 | 383 | 359 | −15 | 3 | 14 | 235 | 249 | −8 | 4 | 15 | 243 | 246 | −6 | 4 | 16 | 459 | 449 |
| −1 | 7 | 13 | 675 | 685 | −13 | 3 | 14 | 270 | 275 | −6 | 4 | 15 | 431 | 454 | −2 | 4 | 16 | 179 | 158 |
| 1 | 7 | 13 | 817 | 827 | −9 | 3 | 14 | 259 | 222 | −4 | 4 | 15 | 271 | 295 | 0 | 4 | 16 | 253 | 234 |
| 3 | 7 | 13 | 530 | 525 | −7 | 3 | 14 | 397 | 374 | 2 | 4 | 15 | 358 | 376 | 2 | 4 | 16 | 194 | 215 |
| 7 | 7 | 13 | 447 | 451 | −3 | 3 | 14 | 165 | 102 | 4 | 4 | 15 | 440 | 454 | −9 | 5 | 16 | 561 | 590 |
| 9 | 7 | 13 | 823 | 822 | 1 | 3 | 14 | 767 | 771 | 6 | 4 | 15 | 326 | 346 | −7 | 5 | 16 | 422 | 432 |
| −12 | 8 | 13 | 298 | 279 | 3 | 3 | 14 | 284 | 326 | 8 | 4 | 15 | 209 | 195 | −5 | 5 | 16 | 295 | 318 |
| −10 | 8 | 13 | 258 | 245 | 7 | 3 | 14 | 212 | 223 | −13 | 5 | 15 | 226 | 196 | −3 | 5 | 16 | 234 | 199 |
| −8 | 8 | 13 | 395 | 418 | 9 | 3 | 14 | 562 | 584 | −7 | 5 | 15 | 358 | 334 | −1 | 5 | 16 | 299 | 307 |
| −6 | 8 | 13 | 280 | 273 | 11 | 3 | 14 | 425 | 439 | −5 | 5 | 15 | 584 | 561 | 1 | 5 | 16 | 312 | 326 |
| 2 | 8 | 13 | 354 | 354 | −18 | 4 | 14 | 264 | 278 | −3 | 5 | 15 | 305 | 273 | −9 | 1 | 17 | 518 | 537 |
| 4 | 8 | 13 | 172 | 169 | −16 | 4 | 14 | 409 | 389 | −1 | 5 | 15 | 516 | 520 | −7 | 1 | 17 | 758 | 808 |
| 6 | 8 | 13 | 262 | 235 | −14 | 4 | 14 | 546 | 547 | 1 | 5 | 15 | 342 | 346 | −5 | 1 | 17 | 205 | 213 |
| −7 | 9 | 13 | 188 | 152 | −10 | 4 | 14 | 480 | 483 | 3 | 5 | 15 | 300 | 295 | 1 | 1 | 17 | 576 | 600 |
| −5 | 9 | 13 | 183 | 157 | −8 | 4 | 14 | 186 | 222 | 5 | 5 | 15 | 449 | 475 | −10 | 2 | 17 | 339 | 336 |
| −3 | 9 | 13 | 219 | 173 | −6 | 4 | 14 | 415 | 406 | −12 | 6 | 15 | 438 | 422 | −8 | 2 | 17 | 964 | 986 |
| −1 | 9 | 13 | 587 | 569 | −4 | 4 | 14 | 354 | 330 | −8 | 6 | 15 | 515 | 518 | −6 | 2 | 17 | 595 | 624 |
| −20 | 0 | 14 | 282 | 272 | 2 | 4 | 14 | 190 | 195 | −6 | 6 | 15 | 375 | 386 | −2 | 2 | 17 | 221 | 259 |
| 18 | 0 | 14 | 473 | 470 | 4 | 4 | 14 | 198 | 197 | −4 | 6 | 15 | 345 | 375 | 0 | 2 | 17 | 857 | 877 |
| 16 | 0 | 14 | 764 | 749 | 8 | 4 | 14 | 174 | 209 | −2 | 6 | 15 | 390 | 414 | 2 | 2 | 17 | 917 | 927 |
| 4 | 0 | 14 | 1155 | 1124 | 10 | 4 | 14 | 428 | 453 | 0 | 6 | 15 | 235 | 210 | −5 | 3 | 17 | 199 | 182 |
| 2 | 0 | 14 | 357 | 325 | −17 | 5 | 14 | 427 | 426 | 2 | 6 | 15 | 178 | 153 | −1 | 3 | 17 | 233 | 235 |
| 0 | 0 | 14 | 264 | 316 | −15 | 5 | 14 | 461 | 453 | | | | | | | | | | |
| −8 | 0 | 14 | 384 | 415 | −13 | 5 | 14 | 384 | 398 | | | | | | | | | | |
| −6 | 0 | 14 | 884 | 871 | −11 | 5 | 14 | 322 | 348 | | | | | | | | | | |
| −4 | 0 | 14 | 1054 | 1032 | −7 | 5 | 14 | 413 | 423 | | | | | | | | | | |
| −2 | 0 | 14 | 265 | 282 | −5 | 5 | 14 | 522 | 536 | | | | | | | | | | |
| 0 | 0 | 14 | 541 | 525 | −3 | 5 | 14 | 541 | 553 | | | | | | | | | | |
| 2 | 0 | 14 | 266 | 269 | −1 | 5 | 14 | 406 | 410 | | | | | | | | | | |
| 4 | 0 | 14 | 604 | 618 | 3 | 5 | 14 | 310 | 336 | | | | | | | | | | |
| 6 | 0 | 14 | 577 | 576 | 5 | 5 | 14 | 329 | 360 | | | | | | | | | | |
| 8 | 0 | 14 | 843 | 882 | 7 | 5 | 14 | 496 | 529 | | | | | | | | | | |
| 10 | 0 | 14 | 852 | 869 | 9 | 5 | 14 | 225 | 270 | | | | | | | | | | |
| 12 | 0 | 14 | 229 | 225 | −14 | 6 | 14 | 449 | 455 | | | | | | | | | | |
| −15 | 1 | 14 | 189 | 143 | −12 | 6 | 14 | 250 | 268 | | | | | | | | | | |
| −7 | 1 | 14 | 446 | 441 | −6 | 6 | 14 | 311 | 302 | | | | | | | | | | |
| −3 | 1 | 14 | 188 | 213 | −4 | 6 | 14 | 446 | 426 | | | | | | | | | | |
| 1 | 1 | 14 | 566 | 550 | −2 | 6 | 14 | 417 | 440 | | | | | | | | | | |
| 3 | 1 | 14 | 327 | 327 | 0 | 6 | 14 | 682 | 673 | | | | | | | | | | |
| 9 | 1 | 14 | 414 | 432 | 2 | 6 | 14 | 388 | 379 | | | | | | | | | | |
| 11 | 1 | 14 | 196 | 193 | 6 | 6 | 14 | 499 | 532 | | | | | | | | | | |
| −16 | 2 | 14 | 336 | 320 | 8 | 6 | 14 | 745 | 778 | | | | | | | | | | |
| −14 | 2 | 14 | 325 | 299 | −13 | 7 | 14 | 195 | 179 | | | | | | | | | | |
| −12 | 2 | 14 | 231 | 232 | −11 | 7 | 14 | 415 | 417 | | | | | | | | | | |
| −4 | 2 | 14 | 343 | 341 | −7 | 7 | 14 | 431 | 417 | | | | | | | | | | |
| −2 | 2 | 14 | 391 | 375 | −5 | 7 | 14 | 428 | 411 | | | | | | | | | | |
| 0 | 2 | 14 | 500 | 497 | −3 | 7 | 14 | 627 | 600 | | | | | | | | | | |
| 2 | 2 | 14 | 251 | 267 | −1 | 7 | 14 | 394 | 391 | | | | | | | | | | |
| 6 | 2 | 14 | 436 | 420 | 1 | 7 | 14 | 256 | 250 | | | | | | | | | | |
| 3 | 7 | 14 | 360 | 332 | −7 | 7 | 15 | 202 | 227 | | | | | | | | | | |
| 5 | 7 | 14 | 376 | 364 | −5 | 7 | 15 | 323 | 322 | | | | | | | | | | |
| −4 | 8 | 14 | 237 | 264 | −3 | 7 | 15 | 553 | 538 | | | | | | | | | | |
| −2 | 8 | 14 | 566 | 565 | −1 | 7 | 15 | 449 | 428 | | | | | | | | | | |
| 0 | 8 | 14 | 416 | 411 | −14 | 0 | 16 | 395 | 401 | | | | | | | | | | |
| −17 | 1 | 15 | 593 | 569 | −8 | 0 | 16 | 578 | 602 | | | | | | | | | | |
| −15 | 1 | 15 | 773 | 752 | −6 | 0 | 16 | 1010 | 1026 | | | | | | | | | | |
| −13 | 1 | 15 | 267 | 266 | −4 | 0 | 16 | 468 | 474 | | | | | | | | | | |
| −7 | 1 | 15 | 547 | 557 | 2 | 0 | 16 | 768 | 793 | | | | | | | | | | |
| −5 | 1 | 15 | 761 | 764 | 4 | 0 | 16 | 461 | 461 | | | | | | | | | | |
| −3 | 1 | 15 | 449 | 469 | −7 | 1 | 16 | 396 | 386 | | | | | | | | | | |
| −1 | 1 | 15 | 473 | 479 | −5 | 1 | 16 | 241 | 230 | | | | | | | | | | |
| 1 | 1 | 15 | 253 | 212 | 1 | 1 | 16 | 383 | 367 | | | | | | | | | | |
| 3 | 1 | 15 | 489 | 496 | 3 | 1 | 16 | 591 | 594 | | | | | | | | | | |
| 5 | 1 | 15 | 552 | 585 | −14 | 2 | 16 | 260 | 263 | | | | | | | | | | |
| 7 | 1 | 15 | 480 | 513 | −8 | 2 | 16 | 355 | 362 | | | | | | | | | | |
| 9 | 1 | 15 | 494 | 490 | −6 | 2 | 16 | 400 | 411 | | | | | | | | | | |
| −12 | 2 | 15 | 329 | 305 | −4 | 2 | 16 | 321 | 336 | | | | | | | | | | |
| −8 | 2 | 15 | 352 | 343 | −2 | 2 | 16 | 194 | 164 | | | | | | | | | | |
| 0 | 2 | 15 | 417 | 405 | 2 | 2 | 16 | 259 | 291 | | | | | | | | | | |
| 4 | 2 | 15 | 496 | 501 | 4 | 2 | 16 | 320 | 348 | | | | | | | | | | |
| 6 | 2 | 15 | 270 | 272 | −11 | 3 | 16 | 166 | 109 | | | | | | | | | | |
| 8 | 2 | 15 | 244 | 279 | −9 | 3 | 16 | 227 | 244 | | | | | | | | | | |
| −11 | 3 | 15 | 205 | 161 | −7 | 3 | 16 | 632 | 666 | | | | | | | | | | |

Significantly, the parent $Mo_2S_4(Et_2NCS_2)_2$ moiety appears as an essentially intact unit in the cluster, with the Mo-Mo bond length decreased very slightly (from 2.814 Å to 2.783 Å) and the Mo-S-Mo bridge angles and bond lengths little changed. However, the dihedral angle between the $MoS_1S_1'$ and $Mo'S_1S_1'$ planes has opened up from 147.9° to 164.4°, and the initially terminal Mo=S bonds have elongated from 2.09 Å to 2.316 Å as their role changes to a bridging $\mu_3$ mode, bound to two Co atoms as well as the original Mo. The binding of two acetonitrile molecules also raises the overall cluster electron count to 60 e−, the predicted number for a stable $M_4$ cluster with six M-M bonds.

EXAMPLE 6

Production of $(Bu_2NCS_2)_2Mo_2(\mu^3\text{-}S)_4Cu_2Cl_2$

A sample of $(i\text{-}Bu_2NCS_2)_2Mo_2S_4$ (100 mg, 0.137 mmol) was dissolved in 15 ml warm $CH_3CN$, and solid CuCl (54 mg, 0.548 mmol) added. The mixture was stirred for 3 minutes, filtered, and the filtrate allowed to stand for 1 hour. The resulting fine red-brown crystalline solid was filtered and dried (yield: 113 mg). Anal. Calc. for $C_{18}H_{36}N_2S_8Mo_2Cu_2Cl_2$: C, 23.33; H, 3.92; N, 3.02; S, 27.67; Mo, 20.70; Cu, 13.71; Cl, 7.65. Found C, 24.38; H, 3.83; N, 3.11; S, 26.82; Mo, 20.51; Cu, 12.94; Cl, 7.55.

Figure 2:
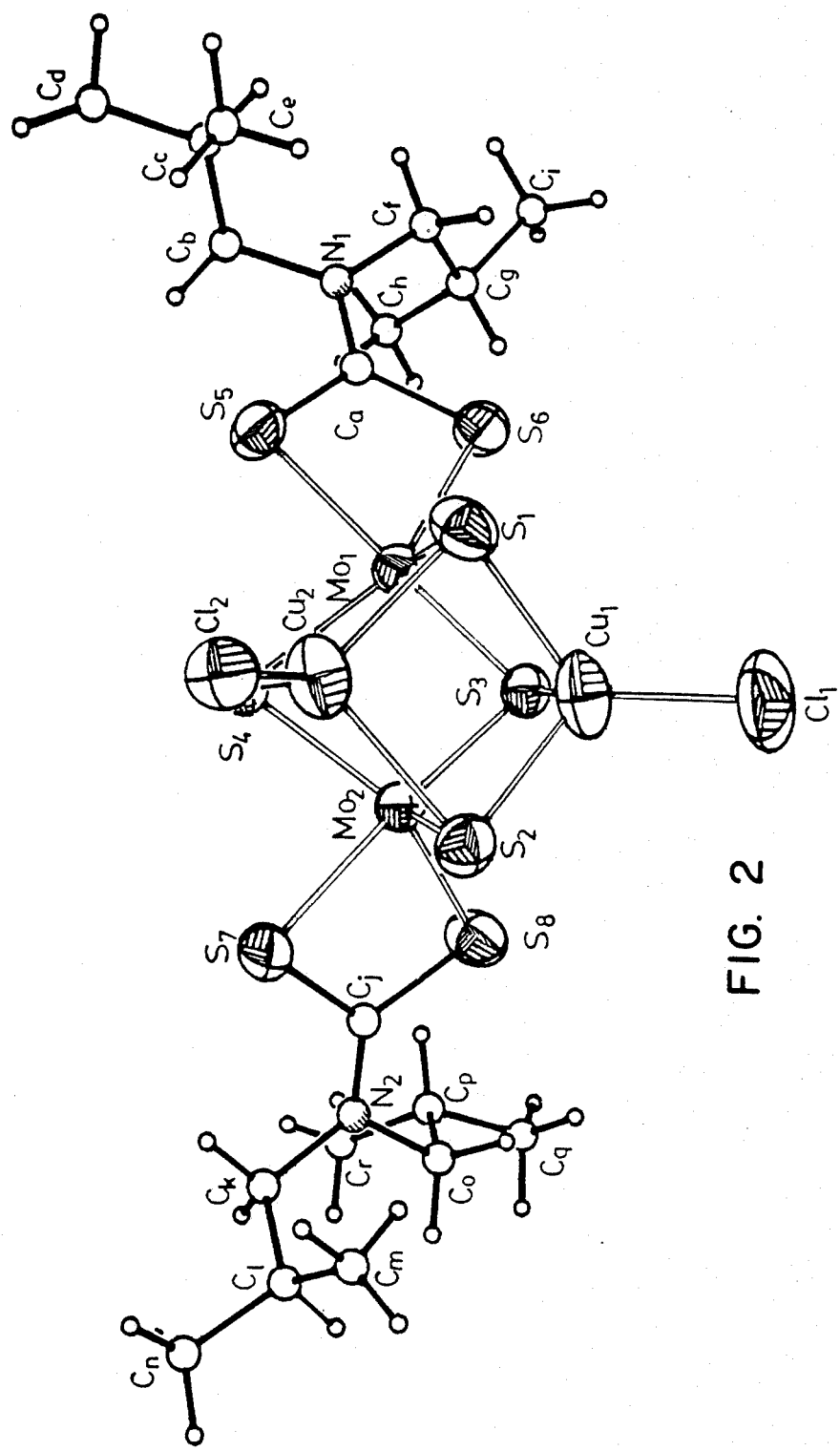
FIG. 2 is a molecular depiction of one composition, i.e., $Mo_2Cu_2(\mu^3-S)_4((C_4H_9)_2NCS_2)_2(Cl)_2$, within the scope of the invention.

A single crystal x-ray diffraction study was carried out on the product. The structure is illustrated in FIG. 2.

EXAMPLE 7

Hydrotreating Catalyst

An amount of the Example 5 material (0.80 gm) was decomposed on a model feed (5% dibenzothiophene/decalin) at 350° C. and 3150 KPa $H_2$ in a modified batch autoclave and gave an extremely high desulfurization rate. A crude zero order rate constant derived from operating data obtained between 2 and 4 hours was determined to be $160 \times 10^{16}$ molecules DBT/g. cat.

precursor/sec. This material was therefore found to be an effective HDS catalyst.

It is to be understood that the above disclosure is by way of specific example and that numerous modifications and variations of the invention are available to those of ordinary skill in the art without departing from the true spirit and scope of the invention.

We claim as our invention:

1. A composition of matter containing a heterometallic thiocubane cluster selected from compositions having the formula $$(M_2^1 M_2^2 S_4) L_2^1 L_2^2 L_2^3,$$

and $$(M_2^1 M_2^2 S_4) L_2^1 L_2^3$$

wherein:
$M^1$ is Re, V, Mo or W,
$M^2$ is Co, Cr, Cu, Ni or Fe,
$L^1$ is a bidentate sulfur and/or nitrogen bearing ligand, and
$L^2$ is a monodentate S, N, P or O donor ligand,
$L^3$ is CO, a monodentate anion ligand selected from halide, mercaptide or alkoxide anion ligands, or O, N, P or S containing monodentate donor ligand, and
wherein $(M_2^1 M_2^2 S_4)$ forms said heterometallic thiocubane cluster.

2. The composition of claim 1 wherein $M^1$ is Mo or W.
3. The composition of claim 1 wherein $M^1$ is Mo.
4. The composition of claim 1 wherein $M^1$ is W.
5. The composition of claim 1 wherein $M^2$ is Co.
6. The composition of claim 3 wherein $M^2$ is Co.
7. The composition of claim 4 wherein $M^2$ is Co.
8. The composition of claim 1 wherein $M^2$ is Cu.
9. The composition of claim 3 wherein $M^2$ is Cu.
10. The composition of claim 4 wherein $M^2$ is Cu.
11. The composition of claim 1 wherein said bidentate ligand, $L^1$, is selected from the group of xanthate, dithiophosphinate, dithiophosphate, o-aminobenzenethiolate, and dithiocarbamate.
12. The composition of claim 1 wherein said bidentate ligand, $L^1$, is $S_2CNR_2$ and wherein R is independently H or a hydrocarbyl group having from 1 to 12 carbon atoms.
13. The composition of claim 12 wherein each R is $C_2H_5$.
14. The composition of claim 2 wherein said bidentate ligand, $L^1$, is $S_2CN(C_2H_5)_2$.
15. The composition of claim 5 wherein said bidentate ligand, $L^1$, is $S_2CN(C_2H_5)_2$.
16. The composition of claim 6 wherein said bidentate ligand, $L^1$, is $S_2CN(C_2H_5)_2$.
17. The composition of claim 7 wherein said bidentate ligand, $L^1$, is $S_2CN(C_2H_5)_2$.
18. The composition of claim 1 wherein said monodentate donor ligand, $L^2$, is acetonitrile.
19. The composition of claim 2 wherein said monodentate donor ligand, $L^2$, is acetonitrile.
20. The composition of claim 14 wherein said monodentate donor ligand, $L^2$, is acetonitrile.
21. The composition of claim 18 wherein said monodentate donor ligand, $L^2$, is acetonitrile.
22. The composition of claim 16 wherein said monodentate donor ligand, $L^2$, is acetonitrile.
23. The composition of claim 17 wherein said monodentate donor ligand, $L^2$, is acetonitrile.
24. The composition of claim 9 wherein said composition has the formula $$(M_2^1 M_2^2 S_4) L_2^1 L_2^3$$

and wherein $L^3$ is Cl.

25. The composition of claim 9 wherein said composition has the formula $$(M_2^1 M_2^2 S_4) L_2^1 L_2^3$$

and wherein $L^3$ is CO.

26. The composition of claim 10 wherein said composition has the formula $$(M_2^1 M_2^2 S_4) L_2^1 L_2^3$$

and wherein $L^3$ is Cl.

27. The composition of claim 10 wherein said composition has the formula $$(M_2^1 M_2^2 S_4) L_2^1 L_2^3$$

and wherein $L^3$ is CO.

* * * * *